US011504329B2

(12) United States Patent
Mathiowitz et al.

(10) Patent No.: US 11,504,329 B2
(45) Date of Patent: Nov. 22, 2022

(54) COMPOSITIONS FOR STABILIZING AND DELIVERING PROTEINS

(71) Applicants: Brown University, Providence, RI (US); TherapyX, Inc., Buffalo, NY (US)

(72) Inventors: Edith Mathiowitz, Brookline, MA (US); Stacia Furtado, Pawcatuck, CT (US); Nejat Egilmez, Louisville, KY (US); Thomas Conway, Hamburg, NY (US)

(73) Assignees: BROWN UNIVERSITY, Providence, RI (US); THEBAPYX, INC., Buffalo, NY (US)

( * ) Notice: Subject to any disclaimer, the term of this patent is extended or adjusted under 35 U.S.C. 154(b) by 100 days.

(21) Appl. No.: 16/909,493

(22) Filed: Jun. 23, 2020

(65) Prior Publication Data

US 2021/0007990 A1   Jan. 14, 2021

Related U.S. Application Data

(63) Continuation of application No. 15/503,891, filed as application No. PCT/US2015/045402 on Aug. 14, 2015, now Pat. No. 10,722,468.

(60) Provisional application No. 62/037,492, filed on Aug. 14, 2014.

(51) Int. Cl.
| | |
|---|---|
| A61K 9/14 | (2006.01) |
| A61K 9/16 | (2006.01) |
| A61K 9/19 | (2006.01) |
| A61K 38/18 | (2006.01) |
| A61K 38/20 | (2006.01) |
| A61K 38/19 | (2006.01) |
| A61K 38/28 | (2006.01) |
| A61K 9/20 | (2006.01) |
| A61K 38/17 | (2006.01) |
| A61K 39/00 | (2006.01) |

(52) U.S. Cl.
CPC ............ *A61K 9/14* (2013.01); *A61K 9/1635* (2013.01); *A61K 9/1641* (2013.01); *A61K 9/1647* (2013.01); *A61K 9/19* (2013.01); *A61K 9/2004* (2013.01); *A61K 38/17* (2013.01); *A61K 38/1841* (2013.01); *A61K 38/1858* (2013.01); *A61K 38/1866* (2013.01); *A61K 38/191* (2013.01); *A61K 38/193* (2013.01); *A61K 38/20* (2013.01); *A61K 38/208* (2013.01); *A61K 38/2066* (2013.01); *A61K 38/28* (2013.01); *A61K 39/00* (2013.01); *A61K 2039/555* (2013.01)

(58) Field of Classification Search
CPC .................................. A61K 9/19; A61K 9/107
See application file for complete search history.

(56) References Cited

U.S. PATENT DOCUMENTS

| | | | |
|---|---|---|---|
| 3,266,987 A | 8/1966 | Crowley | |
| 3,960,757 A | 6/1976 | Morishita | |
| 4,460,563 A | 7/1984 | Calanchi | |
| 4,794,000 A | 12/1988 | Ecanow | |
| 5,019,400 A | 5/1991 | Gombotz | |
| 5,330,768 A | 7/1994 | Park | |
| 6,025,393 A | 2/2000 | Kitano | |
| 6,143,211 A | 11/2000 | Mathiowitz | |
| 6,235,313 B1 | 5/2001 | Mathiowitz | |
| 6,316,029 B1 | 11/2001 | Jain | |
| 6,620,617 B2 | 9/2003 | Mathiowitz | |
| 7,998,477 B2* | 8/2011 | Yakovlevsky | A61P 37/06 424/130.1 |
| 8,673,359 B2 | 3/2014 | Cho | |
| 9,814,553 B1 | 11/2017 | Kleiner | |
| 2001/0000230 A1 | 4/2001 | Bernstein | |
| 2002/0015737 A1* | 2/2002 | Shih | A61K 9/19 424/85.7 |
| 2002/0106406 A1 | 8/2002 | McHugh | |
| 2004/0105821 A1* | 6/2004 | Bernstein | A61P 31/04 424/46 |
| 2005/0152901 A1 | 7/2005 | Pickford | |
| 2008/0124400 A1 | 5/2008 | Liggins | |
| 2009/0202642 A1 | 8/2009 | Huang | |
| 2011/0038855 A1 | 2/2011 | Schoenberger | |
| 2011/0052699 A1 | 3/2011 | Funke | |
| 2012/0021995 A1 | 1/2012 | Bowdish | |
| 2013/0101553 A1 | 4/2013 | Kisseleva | |
| 2014/0199385 A1 | 7/2014 | Steendam | |

FOREIGN PATENT DOCUMENTS

| | | |
|---|---|---|
| GB | 929401 | 6/1963 |
| GB | 929406 | 6/1963 |
| JP | 2008195631 | 8/2008 |
| WO | 9321906 | 11/1993 |
| WO | 9631551 | 10/1996 |
| WO | 0012125 | 3/2000 |
| WO | 0151032 | 7/2001 |
| WO | 2007083316 | 7/2007 |
| WO | 2008070118 | 6/2008 |
| WO | 2013015685 | 1/2013 |
| WO | 2013112456 | 8/2013 |

OTHER PUBLICATIONS

Bataller, et al., "Hepatic stellate cells as target for treatment of liver fibrosis", Semin Liver Dis, 21(03):437-52 (2001).
Bataller, et al., "Liver fibrosis", Clin. Invest., 115(2):209-18 (2005).
Beck, et al., "New long-acting injectable microcapsule contraceptive system," Am J Obstet Gynecol 135(3):419-26 (1979a).

(Continued)

*Primary Examiner* — Kyle A Purdy
(74) *Attorney, Agent, or Firm* — Pabst Patent Group LLP

(57) ABSTRACT

Compositions for stabilizing and delivering proteins and/or other bioactive agents are disclosed. The bioactive agents are embedded or encapsulated in a crystalline matrix. Typically the bioactive agents are in the form of micro- or nanoparticles. The crystalline matrix confers enhanced stability to the agents embedded therein relative to other microparticulate or nanoparticulate bioactive agents. The carriers are especially useful for stabilizing bioactive macromolecules, such as proteins.

18 Claims, 19 Drawing Sheets

(56) References Cited

OTHER PUBLICATIONS

Beck, et al., "A new long-acting injectable microcapsule system for the administration of progesterone," Fertil. Steril., 31:545-51 (1979b).
Beljaars, et al., "Albumin modified with mannose 6-phosphate: A potential carrier for selective delivery of antifibrotic drugs to rat and human hepatic stellate cells", Hepatology, 29:1486-93 (1999).
Beljaars, et al., "Successful targeting to rat hepatic stellate cells using albumin modified with cyclic peptides that recognize the collagen type VI receptor", J Biol Chem., 275:12743-51 (2000).
Benedict, et al., TRAIL: not just for tumors anymore J. Exp. Med., 209(11):1903-6 (2012).
Benita, et al., "Characterization of drug-loaded poly(d,I-lactide) microspheres," J. Pharm. Sci., 73:1721-4 (1984).
Brocchini, et al., "PEGylation of native disulfide bonds in proteins", Nature protocols, 1:2241-52 (2006).
Chae, et al., "Improved antitumor activity and tumor targeting of NH(2)-terminal-specific PEGylated tumor necrosis factor-related apoptosis-inducing ligand.", Molecular cancer therapeutics 9(6):1719-29 (2010).
Cong, et al., "Site-specific PEGylation at histidine tags". Bioconjugate Chemistry, 23(2):248-63 (2012).
Fee, et al., "Size comparison between proteins PEGylated with branched and linear poly(ethylene glycol) molecules", Biotechnol Bioeng., 98(4):725-3 (2007).
Friedman, "Evolving challenges in hepatic fibrosis", Nat Rev Gastroenterol Hepatol. 7(8):425-36 (2010).
Friedman, "Fibrogenic cell reversion underlies fibrosis regression in liver", PNAS, 109(24):9230-1 (2012).
Gong, et al., "Site-specific PEGylation of exenatide analogues markedly improved their glucoregulatory activity", Br J Pharmacol., 163(2):399-412 (2011).
International Search Report for PCT application PCT/IS2015/026513 dated Jun. 7, 2015.
Iredale, et al., "Mechanisms of spontaneous resolution of rat liver fibrosis. Hepatic stellate cell apoptosis and reduced hepatic expression of metalloproteinase inhibitors", J Clin Invest, 102(3):538-49 (1998).
Jonnalagadda, et al., "Effect of the Inclusion of PEG on the Solid-State Properties and Drug Release from Polylactic Acid Films and Microcapsules", Journal of Applied Polymer Science, 93:2025-2030 (2004).
Kim, et al., "A sulfate polysaccharide/TNF-related apoptosis-inducing ligand (TRAIL) complex for the long-term delivery of TRAIL in poly(lactic-co-glycolic acid) (PLGA) microspheres", J Pharm Pharmacol., 65(1):11-21 (2013).
Kim, et al., "Bioimaging for targeted delivery of hyaluronic Acid derivatives to the livers in cirrhotic mice using quantum dots", ACS Nano, 4(6):3005-14 (2010b).
Kim, et al., "Ionic complex systems based on hyaluronic acid and PEGylated TNF-related apoptosis-inducing ligand for treatment of rheumatoid arthritis", Biomaterials, 31(34):9057-64 (2010a).
Kim, et al., "PEGylated TNF-related apoptosis-inducing ligand (TRAIL) analogues: Pharmacokinetics and antitumor effects", Bioconjugate chemistry, 22(8):1631-7 (2011a).
Kim, et al., "PEGylated TNF-related apoptosis-inducing ligand (TRAIL)-loaded sustained release PLGA microspheres for enhanced stability and antitumor activity", J Control Release, 150(1):63¬-9 (2011b).
Kim, et al., "Preparation and characterization of Apo2L/TNF-related apoptosis-inducing ligand-loaded human serum albumin nanoparticles with improved stability and tumor distribution", J Pharm Sci., 100(2):482-91 (2011c).

Lakner, et al., "Inhibitory effects of microRNA 19b in hepatic stellate cell-mediated fibrogenesis", Hepatology, 56(1):300-10 (2012).
Lee, et al., "1004 Treatment with PEGylated TNF-related apoptosis-inducing ligand (TRAIL) induces apoptosis of human rheumatoid arthritis (RA) fibroblast-like synoviocytes (FLS) and suppresses arthritis in murine collagen-induced arthritis", Arthritis and Rheumatism; 72nd Annual scientific meeting of the American college of Rheumatology/43rd annual scientific meeting, Wiley San Francisco, CA, 58(9): Suppl S p. s539, Sep. 1, 2008.
Louis, et al., "Interleukin-10 controls neutrophilic infiltration, hepatocyte proliferation, and liver fibrosis induced by carbon tetrachloride in mic", Hepatology, 28:1607-15 (1998).
Martin-Banderas, et al., "Functional PLGA NPs for Oral Drug Delivery: Recent Strategies and Developments", Mini Reviews in Medical Chemistry, 13:58-69 (2013).
Mathiowitz, et al., "Morphology of polyanhydride microsphere delivery systems" J. Scanning Microscopy, 4:329-40 (1990).
Mathiowitz, et al., "Novel microcapsules for delivery systems," Reactive Polymers, 6:275-83 (1987).
Molineux, "The design and development of pegfilgrastim (PEG-rmetHuG-CSF, Neulasta)", Curr Pharm Des., 10(11):1235-44 (2004).
Newa, et al., "Preparation and Evaluation of Fast Dissolving Ibuprofen-Polyethylene Glycol 6000 Solid Dispersions", Drug Delivery, 15(6):355-364 (2008).
Park, et al., "Down-regulation of FoxO-dependent c-FLIP expression mediates Trail-induced apoptosis in activated hepatic stellate cells", Cell Signal., 21(10):1495-503 (2009).
Pavet, et al., "Multivalent DR5 peptides activate the TRAIL death pathway and exert tumoricidal activity", Cancer Res., 70:1101-10, (2010).
Poelstra, et al., "Drug targeting to the diseased liver", J. Control Release, 161(2):188-97 (2012).
Radaeva, et al., "Natural killer cells ameliorate liver fibrosis by killing activated stellate cells in NKG2D-dependent and tumor necrosis factor-related apoptosis-inducing ligand-dependent manners", Gastroenterology, 130(2):435-52 (2006).
Sawhney, et al., "Bioerodible hydrogels based on photopolymerized poly(ethylene glycol)-co-poly(.alpha hydroxy acid) diacrylate macromers," Macromolecules, 26:581-7 (1993).
Taimr, "Activated stellate cells express the TRAIL receptor-2/death receptor-5 and undergo TRAIL-mediated apoptosis", Hepathology, 37(1):89-95 (2003).
International Search Report for corresponding PCT application PCT/US2015/045402 dated Nov. 17, 2015.
Tur, et al., "DR4-selective tumor necrosis factor-related apoptosis-inducing ligand (TRAIL) variants obtained by structure-based design", J. Biological Chemistry, 283(29):20560-8 (2008).
Van der Sloot, "Designed tumor necrosis factor-related apoptosis-inducing ligand variants initiating apoptosis exclusively via the DR5 receptor", PNAS,103(23):8634-9 (2006).
Wahl, et al., "Increased apoptosis induction in hepatocellular carcinoma by a novel tumor-targeted TRAIL fusion protein combined with bortezomib", Hepatology, 57(2):625-36 (2013).
Wang, et al., "Small-molecule activation of the TRAIL receptor DR5 in human cancer cells", Nature Chemical Biology, 9:84-9 (2013).
Yang, et al., "Target specific hyaluronic acid-interferon alpha conjugate for the treatment of hepatitis C virus infection", Biomaterials, 32(33):8722-9 (2011).
Zhu, et al., "Evaluation of the Microstructure of Semicrystalline Solid Dispersions", Molecular Pharmaceutics, 7(4):1291-1300 (2010).

\* cited by examiner

COMPOSITIONS FOR STABILIZING AND DELIVERING PROTEINS

CROSS REFERENCE TO RELATED APPLICATIONS

This application claims priority to U.S. Provisional Patent Application No. 62/037,492 filed Aug. 14, 2014, incorporated herein by reference.

STATEMENT REGARDING FEDERALLY SPONSORED RESEARCH

This invention was made with government support under R21 AI092133, R01 CA100656, and R44 AI080009 awarded by the National Institutes of Health. The Government has certain rights in the invention.

FIELD OF THE INVENTION

The invention is generally directed to compositions for stabilizing bioactive agents, particularly proteins, and delivery thereof.

BACKGROUND OF THE INVENTION

The use of microparticles and nanoparticles as carriers for drugs and other bioactive agents is well known in the art. Microsphere and nanosphere-based polymeric systems have great potential for drug delivery systems due to their ability to shield active agents from external solvents and degradants. Such systems are especially useful in the context of oral drug delivery due to their ability to protect active agents from the harsh gastrointestinal tract.

For example, U.S. Pat. No. 8,673,359 to Cho, et al., describes nanoparticles made using various bioadhesive polymers having enhanced intestinal uptake in vivo. The particles may also contain between 5 to 20 weight percent hydrophilic polymeric material.

Although significant effort has focused on developing effective delivery systems for clinical use, significant obstacles exist in the development of effective systems for drug delivery. There remains a need for improved compositions and methods for stabilizing bioactive agents, particularly proteins, which allow the agents to be administered orally.

Therefore, it is an object of the invention to provide compositions that confer a high degree of stability to the bioactive active agents contained therein.

It is a further object of the invention to provide compositions capable of passing through the stomach without substantial degradation.

It is another object of the invention to provide compositions capable of delivering bioactive agents to specific tissue systems with higher selectivity than the compositions of the prior art.

It is yet a further object of the invention to provide methods for making and using such compositions.

SUMMARY OF THE INVENTION

Disclosed herein are compositions for the delivery of bioactive agents. The compositions contain a crystalline matrix that provides enhanced storage stability for bioactive agents relative to the particles disclosed in the prior art. The bioactive agents are embedded in the matrix, effectively shielding them from environments that promote degradation. The matrix may be used to stabilize bioactive agents, such as biologic drugs and vaccines.

Because the matrix is able to pass through the stomach after oral administration without substantial degradation, it can administer proteins and other drugs that are susceptible to degradation either by the peptidase enzymes or low pH found in the stomach. As shown by the data, following oral administration, the matrix is preferentially absorbed by the Peyer's patches and mesenteric lymph nodes found in the small intestine. Agents entrapped in the matrix may be delivered either locally to tissues along the gastrointestinal tract, or may be delivered systemically, depending on the presence or absence of other polymers in the composition.

BRIEF DESCRIPTION OF THE DRAWINGS

FIG. 4D depicts weight loss (y-axis depicts weight percent relative to starting weight, x-axis depicts age in weeks) associated with administration of IL-10 loaded particles relative to placebo in mice (n=4 for wild type (black circles), 6 for control (white circles) and 6 for IL-10 (grey circles)). Statistical comparison was made between Control and IL10-treated groups. FIG. 4E depicts survival rate for mice that received IL-10 loaded particles (white circles) relative to control mice (black circles) (y-axis depicts percentage of mice alive, x-axis depicts mice age in days). Mortality was determined for APCmin/+ mice receiving either no treatment (control), or chronic IL-10 microsphere treatment (n=13 and 11, respectively). In FIGS. 4A-E,

*, , *, ****=p<0.05, p<0.01, <0.001, and <0.0001, respectively. Error bars, s.e.m.

Figure 5A:
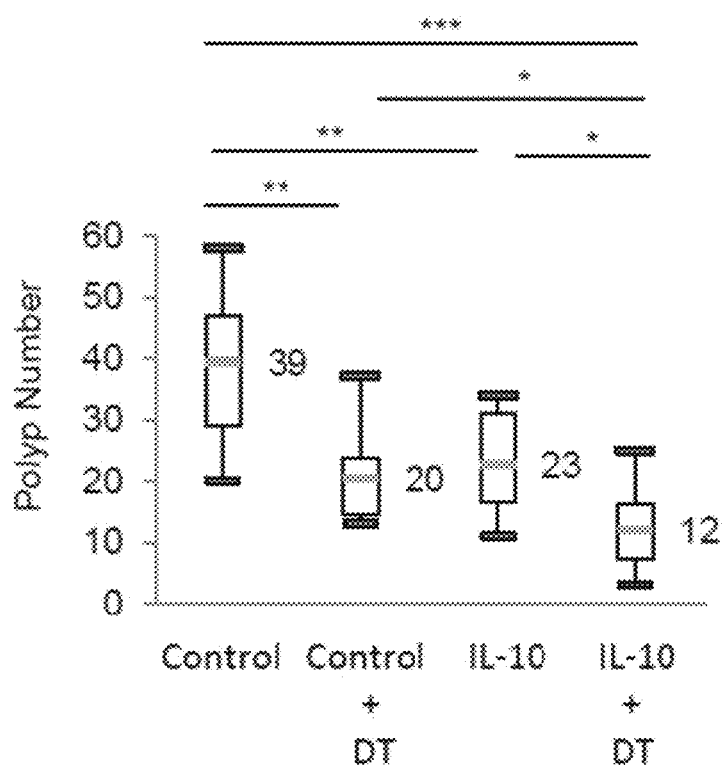
Figure 5B:
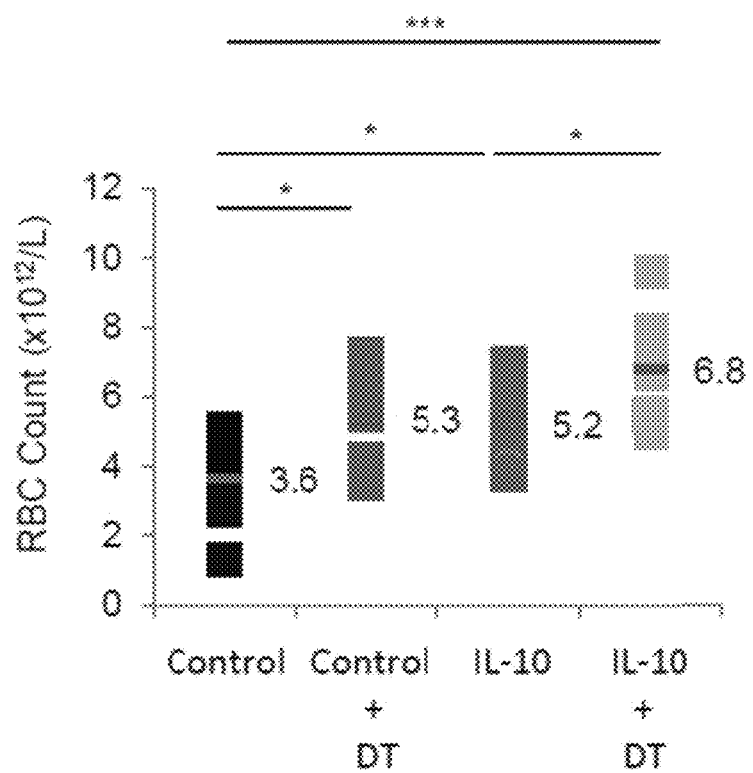
Figure 5C:
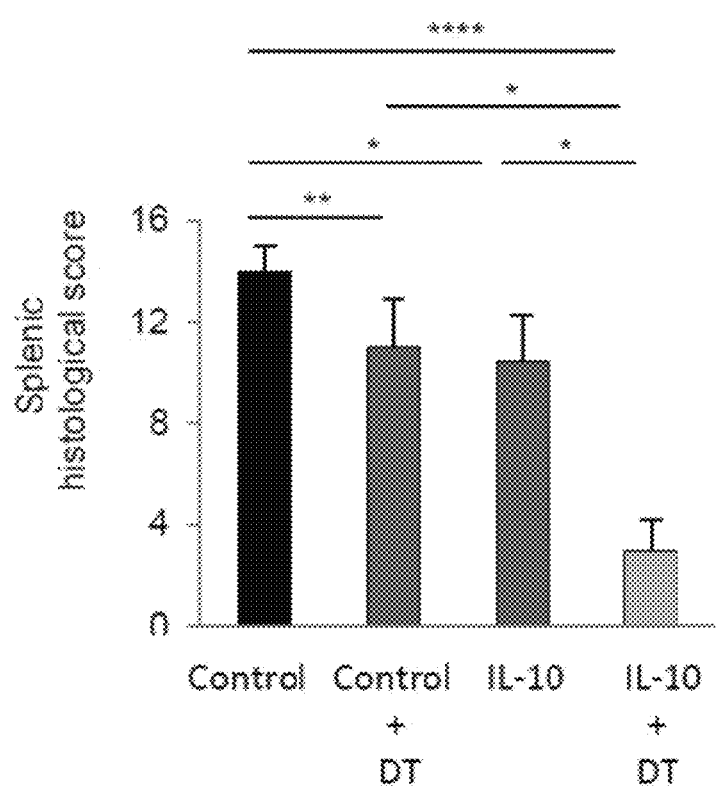

FIGS. 5A-C depict reduced polyp burden (FIG. 5A, y-axis depicts number of polyps), anemia (FIG. 5B; y-axis depicts RBC count ($\times 10^{12}$/L)) and splenic pathology scores (FIG. 5C; y-axis depicts splenic histology score) in Treg depleted mice (n=4-5) receiving IL-10 loaded particles. Ten week-old APC min/+−DEREG mice received either mock (PBS) or subtotal Treg depletion (DT), concomitant with either Control or IL-10 microparticle therapy. Disease markers were quantified at the end of the therapeutic period. In each of FIGS. 5A-C, the left most dataset corresponds to control mice (Control), the second dataset corresponds to control+Treg depleted mice (Control+DT), the third dataset corresponds to mice receiving IL-10 particles (IL-10), and the right most dataset corresponds to Treg-depleted mice receiving IL-10 particles (IL-10+DT). In FIGS. 5A-C, n=7-8; *, , *, ****=p<0.05, p<0.01, <0.001, p<0.0001, respectively; Error bars, s.e.m.

Figures 6A, 6B:
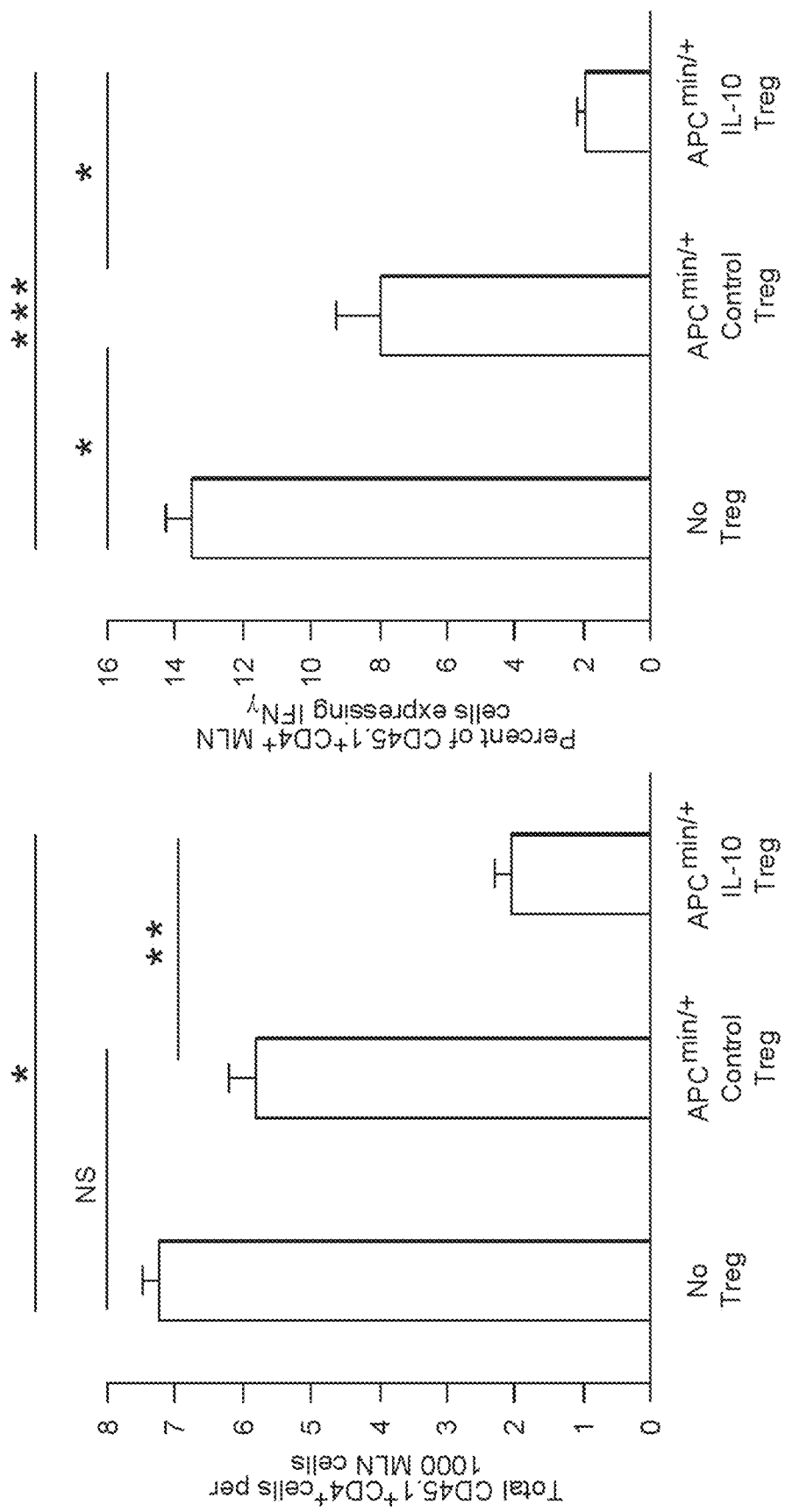

FIGS. 6A-B depict suppression of T-cell activation (FIG. 6A; y-axis depicts total CD45.1$^+$CD4$^+$ cells per 1000 MLN cells) and proliferation (FIG. 6B; y-axis depicts percent CD45.1$^+$CD4$^+$MLN cells expressing IFNγ) by treatment of mice with IL-10 loaded particles. In both FIGS. 6A-B, the left hand dataset corresponds to mice without Treg depletion (no Treg), the middle set corresponds to mice with Treg depletion (APC$^{min/+}$Control Treg) and the right dataset corresponds to mice with Treg depletion receiving IL-10 (APC$^{min/+}$IL-10 Treg). For FIGS. 6A-B, n=4-5; *, , *=p<0.05, p<0.01, and <0.001, respectively; Error bars, s.e.m.

Figures 7A, 7B:
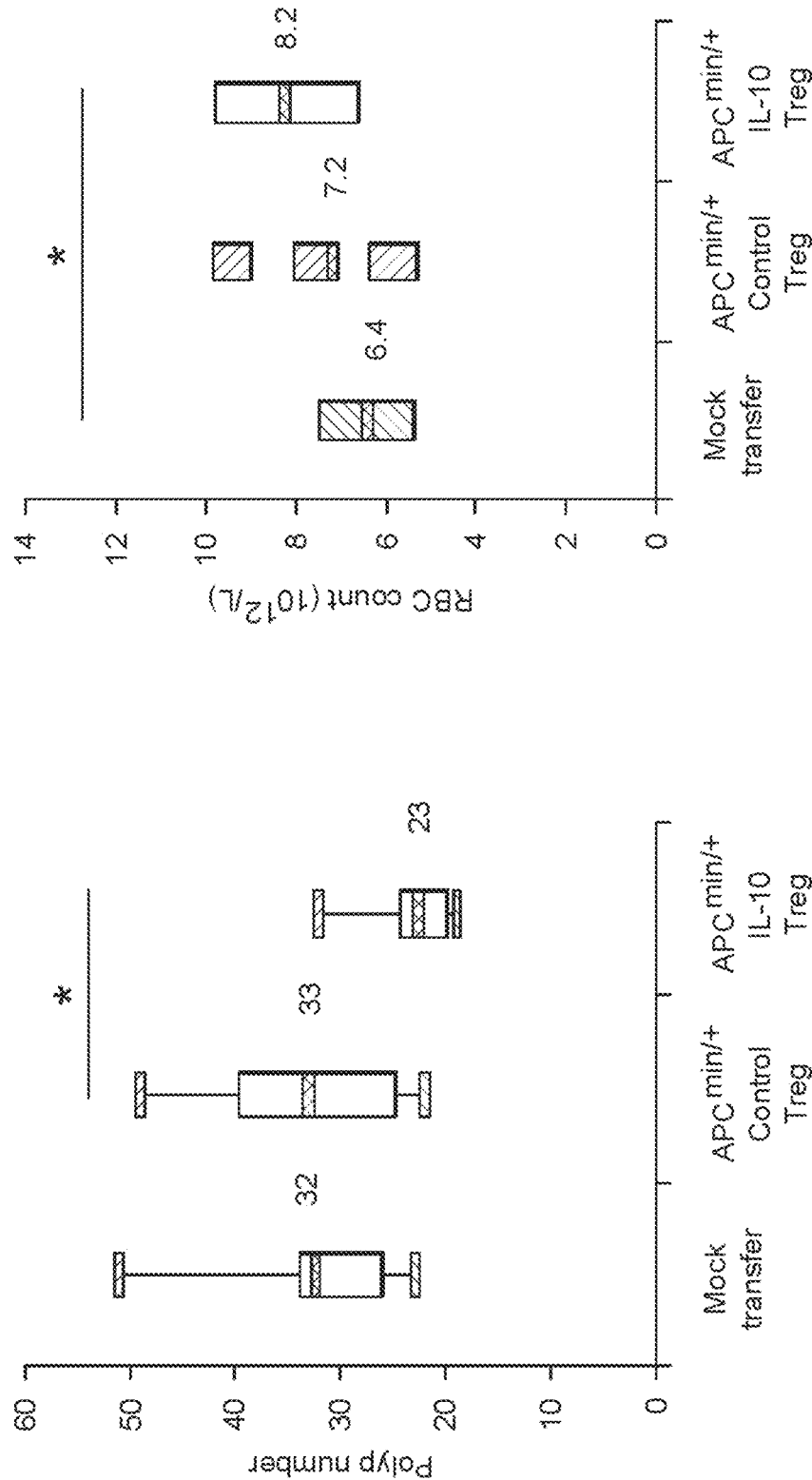
Figure 7C:
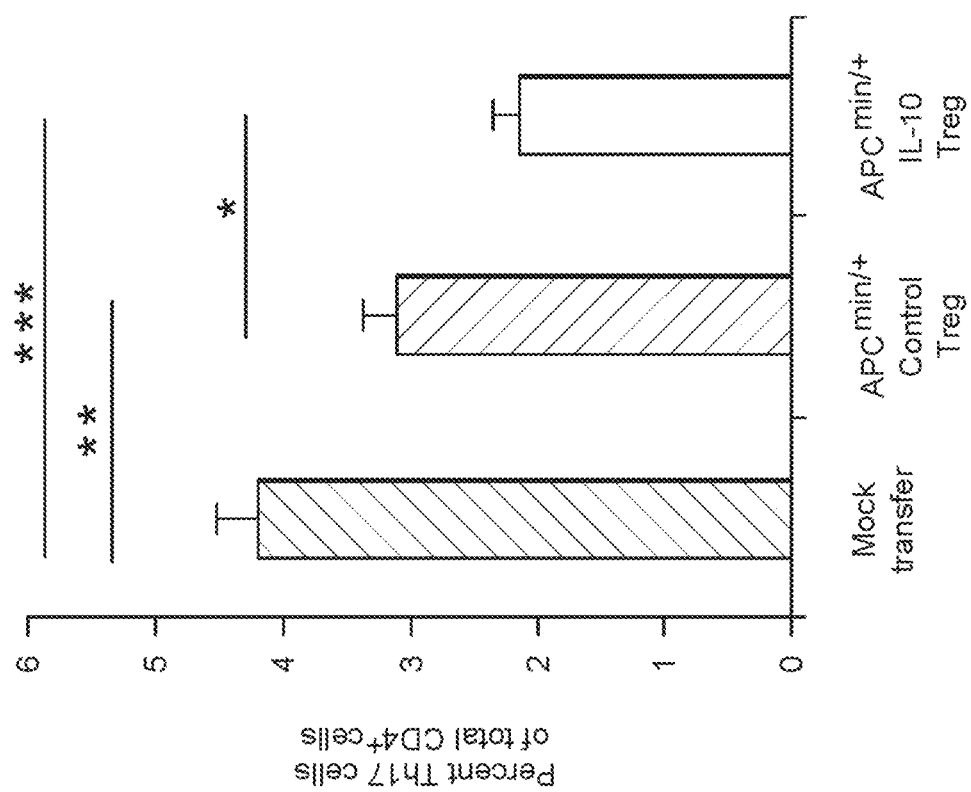

FIGS. 7A-7C depict reduced polyposis (FIG. 7A; y-axis depicts number of polyps), corrected anemia (FIG. 7B; y-axis depicts RBC count ($\times 10^{12}$/L) and decreased Th17 (FIG. 7C; y-axis depicts percent of Th17 cells of total CD4+ cells) in mice transplanted with cells from a mouse receiving IL-10 loaded particles. In each of FIGS. 7A-C, the left most dataset corresponds to mock transfer mice (n=4) (Mock Transfer), the second dataset corresponds to mice receiving cells from Treg depleted mice (n=8) (APC$^{min/+}$Control Treg), the third dataset corresponds to mice receiving cells from Treg depleted mice previously treated with IL-10 particles (n=8) (APC$^{min/+}$IL-10 Treg). For FIGS. 7A-C, *, , *=p<0.05, p<0.01, and <0.001, respectively; Error bars, s.e.m.

Figure 8A:
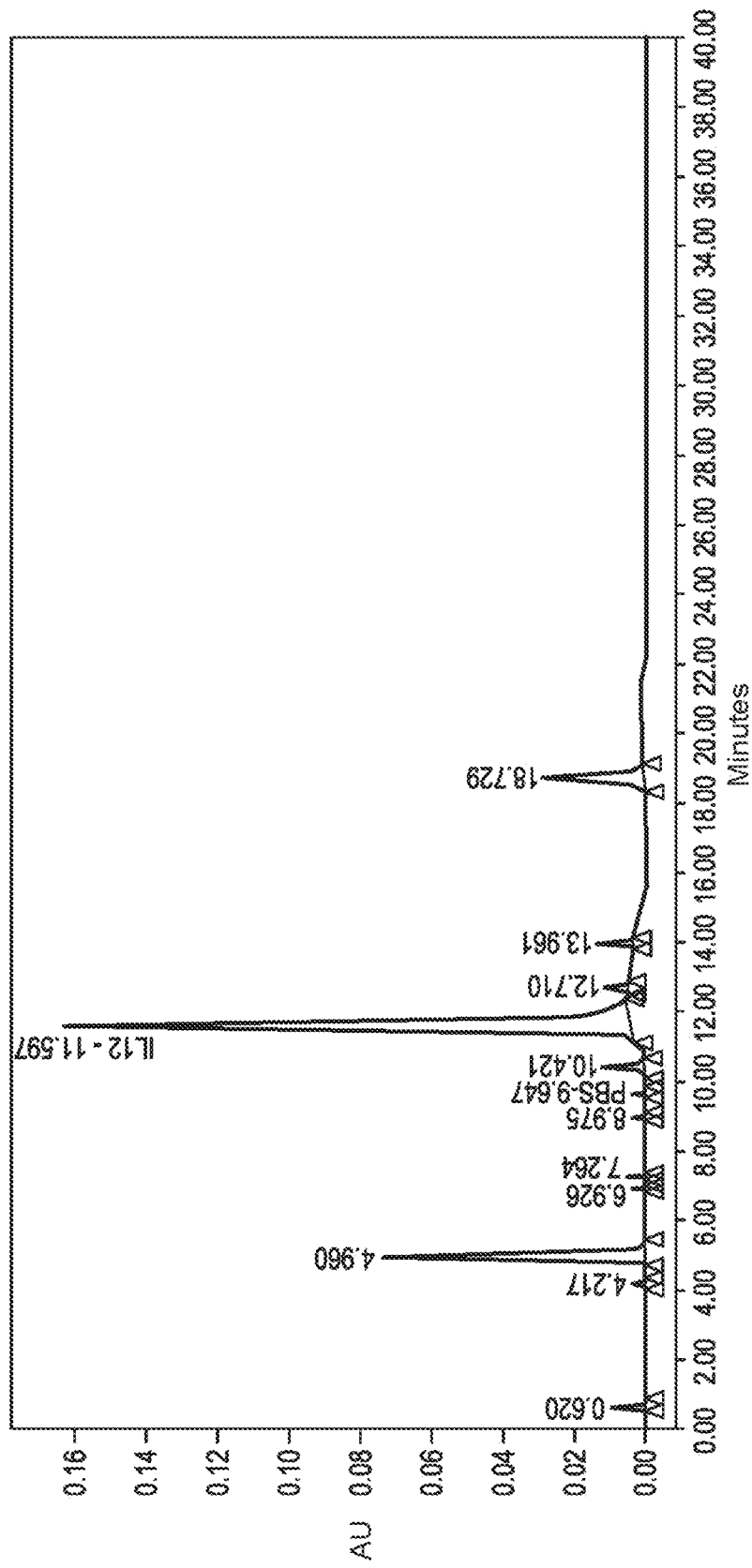
Figure 8B:
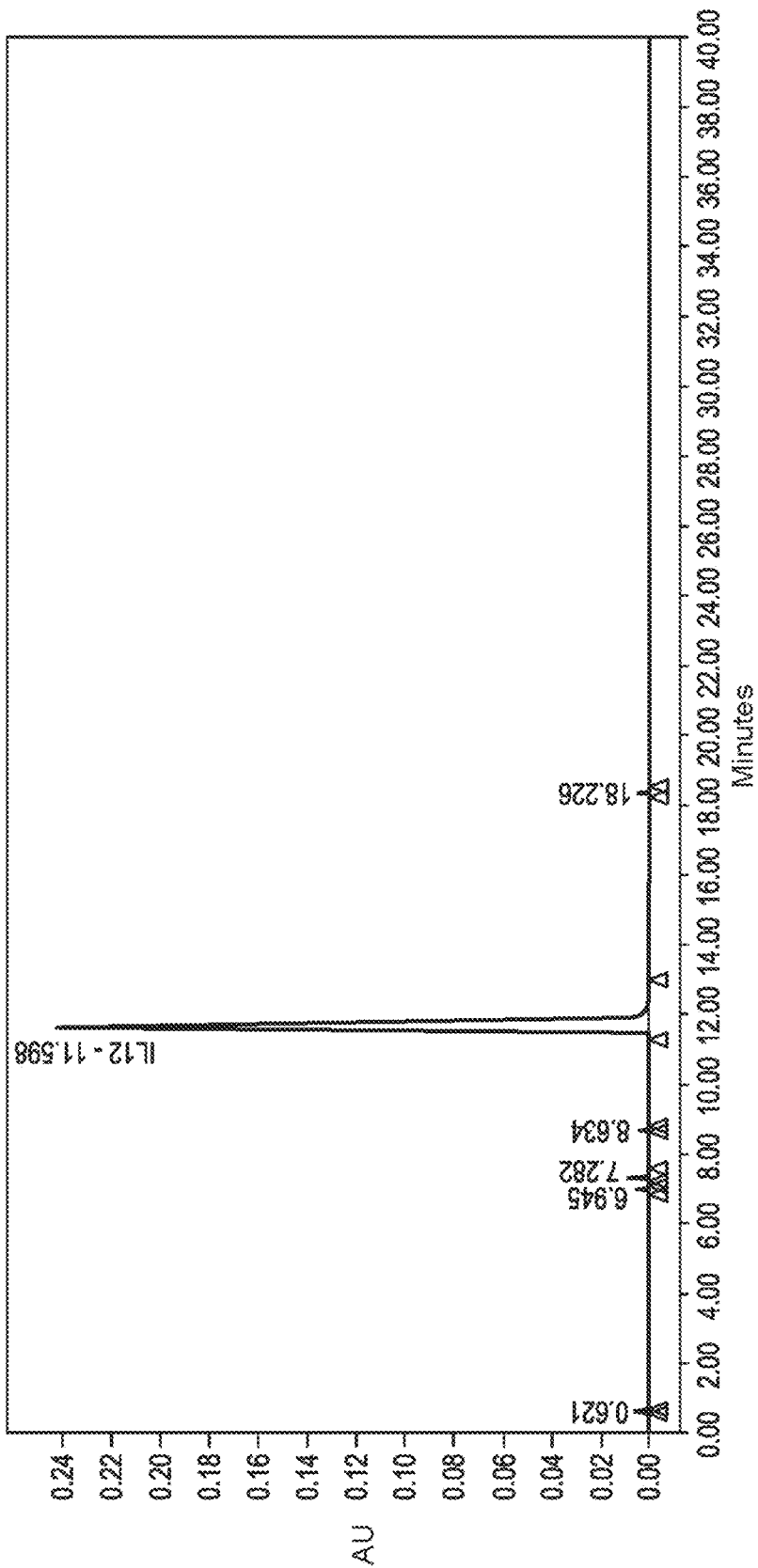

FIGS. 8A and 8B are chromatograms from pure IL-12 and IL-12 extracted from a matrix particle, respectively.

Figure 9:
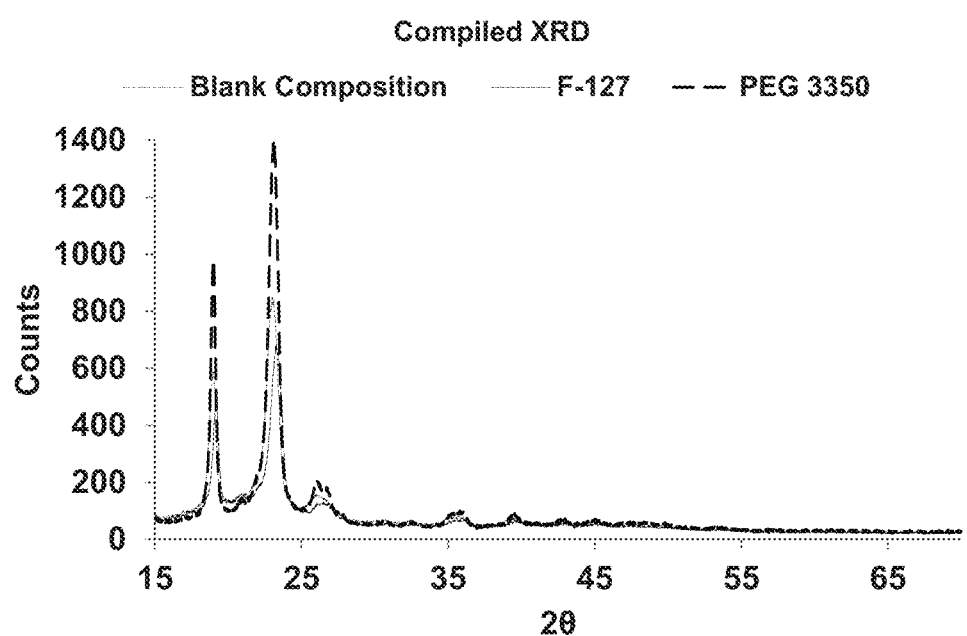

FIG. 9 depicts a PXRD overlay of pure PEG 3350, Pluronic® F127, and blank matrix particles formed by a bench scale process.

Figure 10:
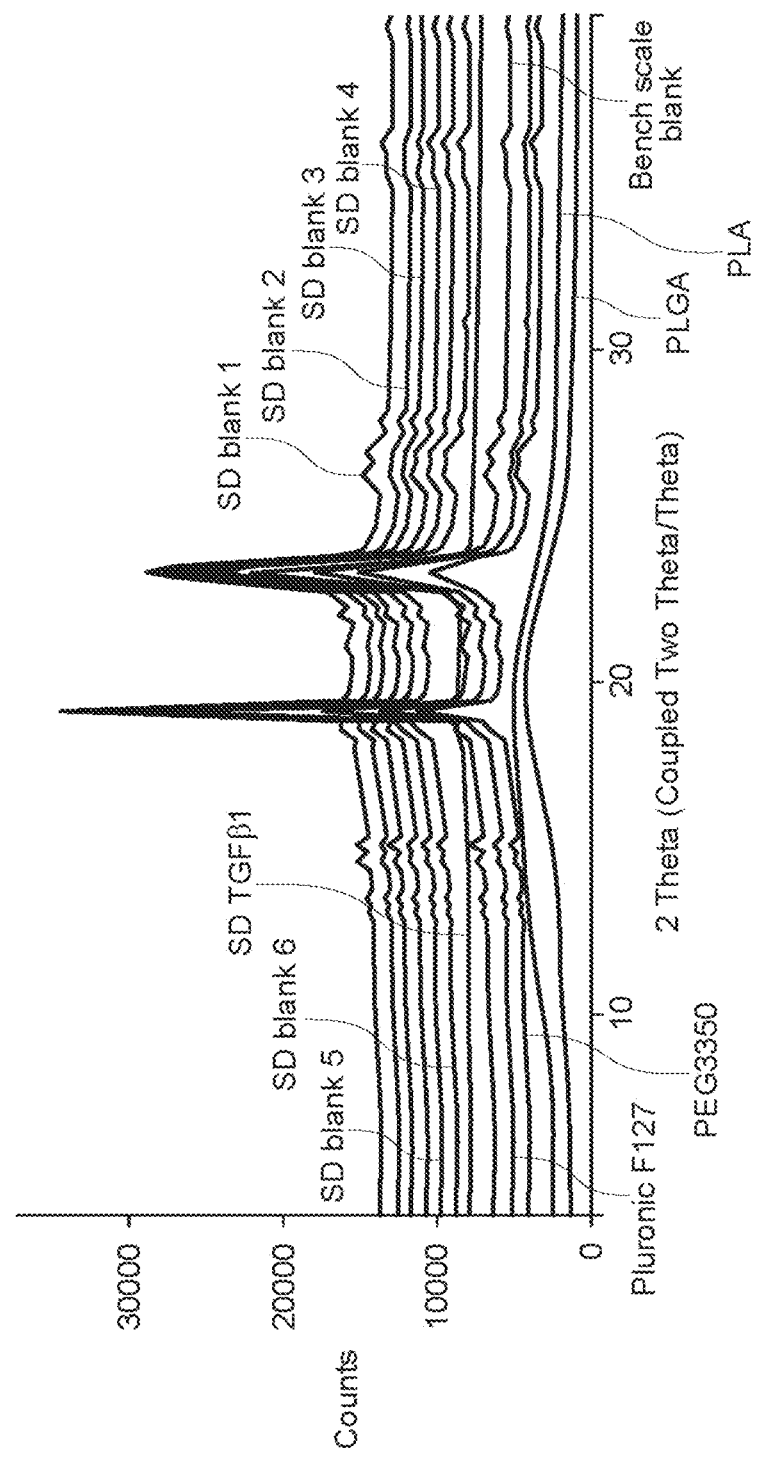

FIG. 10 depicts a PXRD overlay of six batches of blank spray dried particles (SD blank 1, SD blank 2, SD blank 3, SD blank 4, SD blank 5, and SD blank 6), one batch of spray dried particles containing TGFβ1 (SD TGFβ1), blank matrix particles formed by a bench scale process involving a lyophilization step followed by a filtration and recovery step (precipitation) (bench scale blank), Pluronic® F127, PEG 3350, polylactic acid (PLA), and poly(lactide co-glycolide) (PLGA).

DETAILED DESCRIPTION OF THE INVENTION

I. Definitions

As used herein, the terms "matrix" and "matrix-element" refer to a three-dimensional network of polymeric compounds. The polymeric compounds are arranged in such a way as to permit the inclusion of other compounds inside the three dimensional network.

As used herein, the term "matrix-forming polymer" refers to a polymer which is capable of forming a semi-crystalline matrix. The matrix-forming polymer is crystallizable, meaning that it is capable of existing in a semi-crystalline state.

As used herein, "semi-crystalline polymer" refers to a polymer containing both amorphous and crystalline phases, where 2-99%, and integer values there between, of the polymer chains are oriented or aligned in a regular array. In practice, a polymer's morphology never achieves 100% crystallinity, i.e. where all of the polymer chains are aligned in a regular array. Rather, a polymer includes segments in which some of the polymer chains are in a random or disorganized state, known as the amorphous phase, while other polymer chains are aligned in a regular array. The degree to which the polymer chains are oriented or aligned in a regular array is known as "percent crystallinity." Percent crystallinity can be determined using standard methods, such as differential scanning calorimetry (DSC) and powder X-ray diffraction (PXRD), or a combination of two methods, such as a combination of DSC and PXRD, which allows for the determination of heat of fusion values for theoretical 100% crystalline polymers.

A semi-crystalline polymer or matrix is characterized by PXRD as containing one or more sharp peaks, such as shown in FIG. 9. Semi-crystalline polymers and matrices characterized by DSC show a glass transition temperature, melting point, and heat of fusion.

In contrast, when amorphous polymers or matrices are characterized by PXRD, the resulting graph contains humps, without any distinct peaks, such as shown for PLGA in FIG. 10. Amorphous polymers and matrices characterized by DSC only have a glass transition temperature. DCS does not show any inciting point or heat of fusion for an amorphous polymer.

"Semi-crystalline matrices" as used herein refers to matrices that contain both amorphous and crystalline phases, such as described above with respect to "semi-crystalline polymers."

"Water soluble" can be used to refer to one or more polymers that form the matrix. In this context, water soluble means at least 0.01% w/v of the polymer is dissolved in water or an aqueous solvent and neutral pH, room temperature and atmospheric pressure.

"Biocompatible" and "biologically compatible", as used herein, refer to materials that are, along with any metabolites or degradation products thereof, generally non-toxic to the recipient, and do not cause any significant adverse effects to the recipient, at concentrations resulting from the degradation of the administered materials. Generally speaking, biocompatible materials are materials that do not elicit a significant inflammatory or immune response when administered to a patient.

"Biodegradable polymer" as used herein, generally refers to a polymer that will degrade or erode by enzymatic action or hydrolysis under physiologic conditions to smaller units or chemical species that are capable of being metabolized, eliminated, or excreted by the subject. The degradation time is a function of polymer composition, morphology, such as porosity, particle dimensions, and environment.

"Mean particle size" as used herein, generally refers to the statistical mean particle size (diameter) of the particles in the composition. Two populations can be said to have a "substantially equivalent mean particle size" when the statistical mean particle size of the first population of particles is within 20% of the statistical mean particle size of the second population of particles; more preferably within 15%, most preferably within 10%.

As used herein, the term "microparticle" generally refers to a particle having a diameter, from about 1 micron to about 100 microns, preferably from about 1 to about 50 microns, more preferably from about 1 to about 30 microns, most preferably from about 1 micron to about 10 microns. The microparticles can have any shape. Microparticles having a spherical shape may be referred to as "microspheres."

As used herein, the term "nanoparticle" generally refers to a particle having a diameter, from about 1 nanometer to 1000 nanometers, preferably from about 10 nanometers to 1000 nanometers, more preferably from about 100 nanometers to 1000 nanometers, most preferably from about 250 nanometers to 1000 nanometers. The nanoparticles can have any shape. Nanoparticles having a spherical shape may be referred to as "nanospheres."

II. Compositions

The compositions include a matrix and a bioactive agent. The matrix is configured to stabilize the bioactive agent, protecting it from degradation by enzymes and/or acidic pH. The matrix is made from at least one semi-crystalline water soluble polymer. Generally, the matrix contains one or more semi-crystalline polymers present in an amount of at least 30% wt/wt. In preferred embodiments, a bioactive agent is entrapped, entrained or otherwise associated with the matrix. The bioactive agent is typically in microparticulate or nanoparticulate form.

The matrix can have any form, but is typically in the form of a plurality of particles. The particles may be of any suitable size for the desired delivery method. Preferably, the diameter of the particles is from 1 nm to 1000 μm, more preferably from 100 nm to 1000 μm, and even more preferably from 1 to 1000 μm.

Particle size analysis can be performed on a Coulter counter, by light microscopy, scanning electron microscopy, transmittance electron microscopy, laser diffraction methods such as those using a Malvern Mastersizer, light scattering methods or time of flight methods. As used herein "Coulter method" refers to a method in which the powder is dispersed in an electrolyte, and the resulting suspension analyzed using a Coulter Multisizer II fitted with a 50-μm aperture tube. This method provides size measurements and particle concentrations.

The composition may also contain one or more additional biocompatible polymers. The other biocompatible polymers may be part of the matrix or separate from the matrix. The additional polymers may be non-crystalline (amorphous) or semi-crystalline. The additional polymers may be biodegradable, bioerodible and/or bioadhesive.

The composition may also contain one or more stabilizing agents, encapsulating agents and dyes or any combination thereof.

A. Matrix

1. Semi-Crystalline, Water Soluble Polymer

The matrix includes at least one matrix forming polymer, which is a semi-crystalline, water soluble polymer. As used herein, the term "matrix forming polymer" includes single polymers and mixtures of two or more polymers. Representative matrix forming polymers include, but are not limited to, polyalkylene glycols, polyalkylene oxides, poloxamers, polyvinyl alcohols, hydroxyalkyl celluloses, carrageenans, and co-polymers thereof. Other semi-crystalline, water soluble polymers include, but are not limited to, polyvinyl alcohol, polyoxyethylene alkyl ethers, polysorbates, polyoxyethylene-fatty acid copolymers and alginates. Representative polyoxyethylene-fatty acid copolymers include, but are not limited to, polyoxyethlene mono- and di-stearates.

As shown in the Examples, the resulting matrix is semi-crystalline even after film casting with different polymers (e.g., PLA, PLGA, P(FASA), PS, and/or PCL). When amorphous polymers such as PLA (poly(lactic acid)), P(FASA) (poly(fumaric co-sebacic anhydride)) and polystyrene are dissolved and mixed with the matrix forming polymer(s) and then are either solvent cast, or fabricated by any other way to evaporate the solvent, such as precipitation, such as described, in Example 1, or spray dried (see Example 13), the resulting matrix is semi-crystalline. This was demonstrated by the existence of melting point of at least one of the matrix forming polymers, the existence of the heat of fusion, and PXRD analysis.

As shown herein, matrices made with PEG are semi-crystalline with a $T_M$ of about 60° C. and a heat of fusion of about 73 J/g. Matrices made with F127 are semi-crystalline with a $T_M$ of about 49° C. and a heat of fusion of about 47 J/g. The $T_M$ and heats of fusion of PEG, F127 and mixtures containing these polymers can be compared to ascertain differences in the crystallinity of the samples. In PXRD each phase produces a unique diffraction pattern. Suitable software packages can be used to separate the regularly arranged phase from the amorphous phases in a diffraction graph. The total area of each diffracted pattern is determined. The degree of crystallinity is determined by dividing the area of the diffracted pattern of the regularly arranged phase by the sum of the areas of both phases. The diffraction patterns of PEG, F127 and mixtures containing these polymers can be compared to ascertain differences in the crystallinity of the samples, i.e. determine whether the matrix containing these polymers is semi-crystalline, or amorphous.

One can determine whether a matrix is amorphous or semi-crystalline using DSC, PXRD, or both. For example, a semi-crystalline matrix, is characterized by PXRD as containing one or more sharp peaks, which correspond with the semi-crystalline and crystalline materials that form the matrix. Semi-crystalline matrices can also be characterized by DSC with a glass transition temperature, melting point, and heat of fusion.

In contrast, an amorphous matrix is characterized by a PXRD scan as containing humps, without any distinct peaks, as shown with the PLGA sample in FIG. 10. And an amorphous matrix is characterized by DSC with only a glass transition temperature, but no melting point, or heat of fusion.

Percent crystallinity can also be determined using standard methods, such as differential scanning calorimetry (DSC) and powder X-ray diffraction (PXRD), or a combination of two methods, such as a combination of DSC and PXRD, which allows for the determination of heat of fusion values for theoretical 100% crystalline polymers, and the calculation of percent crystallinity. The percent crystallinity of the matrix can be between 2-99%, 5-90%, 5-80%, 5%-70%, 10-90%, 10-80%, 10-70%, 15-90%, 15-80%, 15-70%, 20-90%, 20-80%, 20-70%, 25-90%, 25-80%, 25-70%, 30-90%, 30-80%, or 30-70%. Preferably, the crystallinity of the matrix ranges from 10-80%, more preferably from 20 to 70%.

In certain preferred embodiments, the polyalkylene glycol has an average molecular weight ranging from 200 to 10,000 Daltons, preferably from 500 to 5,000 Daltons, more preferably from 1,000 to 5,000 Daltons, and even more preferably from 2,000 to 4,500 Daltons. Preferably the polyalkylene glycol is polyethylene glycol (PEG). Particularly preferred. PEGs include PEG 3000, 3250, 3350, 3500, 3750, 4000, and 4500.

The matrix forming polymer may be a copolymer, preferably a block copolymer. Exemplary block copolymers include mixtures of polyethylene glycol and polypropylene glycol. Preferred block copolymers include poloxamers (i.e. block copolymers having a central polypropylene glycol chain connected on each end to a polyethylene glycol chain). These polymers are typically sold under the trade names SYNPERONIC®, PLURONIC®, and KOLLIPHOR®. Especially preferred poloxamer compounds include PLURONIC® F127.

The matrix may include two or more matrix forming polymers. In certain embodiments, the matrix includes at least one polyethylene glycol and at least one poloxamer. In an especially preferred embodiment, the matrix includes PEG 3350 and/or PEG 4500 and PLURONIC® F127.

Generally, the matrix forming polymer is solid at room temperature, has a melting point of at least 40° C., and is characterized by a heat of fusion of at least 15 J/g. In other embodiments, the heat of fusion is at least 20 J/g, preferably 25 J/g, more preferably 30 J/g.

Generally, the matrix forming polymer is characterized by a water solubility of at least 50% w/w at room temperature and standard pressure. In certain embodiments, the water solubility is between 50-80% w/w at room temperature, and in other embodiments, the matrix forming polymer is completely soluble (100% w/w) in water at room temperature and standard pressure.

Generally, the semi-crystalline polymer constitutes at least 30% by weight of the matrix. In certain preferred embodiments, the semi-crystalline polymer constitutes at least 35%, 40%, or 50% by weight of the matrix, and even more preferably constitutes at least 65% by weight of the matrix. In an especially preferred embodiment, the semi-crystalline polymer constitutes at least 75% by weight of the matrix.

B. Bioactive Agents

The matrix may contain a bioactive agent. Exemplary classes of bioactive agent include therapeutic, prophylactic and diagnostic agents. For example, the bioactive agent may be a small molecule drug, a biologic drug, a vaccine, a protein, an antibody or other biological macromolecule. The bioactive agent may be a mixture of two or more different compounds, such as those listed above.

Exemplary bioactive agents that can be incorporated into the matrix include, but are not limited to, tumor antigens, CD4+ T-cell epitopes, cytokines, chemotherapeutic agents, radionuclides, small molecule signal transduction inhibitors, photothermal antennas, monoclonal antibodies, immunologic danger signaling molecules, other immunotherapeutics, enzymes, antibiotics, antivirals (especially protease inhibitors alone or in combination with nucleosides for treatment of HIV or Hepatitis B or C), anti-parasites (helminths, protozoans), growth factors (e.g. members of the TGFβ superfamily), growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, immunomodulators (including ligands that bind to Toll-Like Receptors (including but not limited to CpG oligonucleotides) to activate the innate immune system, molecules that mobilize and optimize the adaptive immune system, molecules that activate or up-regulate the action of cytotoxic T lymphocytes, natural killer cells and helper T-cells, and molecules that deactivate or down-regulate suppressor or regulatory T-cells), agents that promote uptake of microparticles into cells (including dendritic cells and other antigen-presenting cells), nutraceuticals such as vitamins, and oligonucleotide drugs (including DNA, RNAs, antisense, aptamers, small interfering RNAs ribozymes, external guide sequences for ribonuclease P, and triplex forming agents).

Exemplary diagnostic agents include paramagnetic molecules, fluorescent compounds, magnetic molecules, and radionuclides, x-ray imaging agents, and contrast agents.

The bioactive agent may be one or more immunomodulatory agents. Exemplary immunomodulatory agents include cytokines, xanthines, interleukins, interferons, oligodeoxynucleotides, glucans, growth factors (e.g., TNF, CSF, GM-CSF and G-CSF), hormones such as estrogens (diethylstilbestrol, estradiol), androgens (testosterone, HALOTESTIN® (fluoxymesterone)), progestins (MEGACE® (megestrol acetate), PROVERA® (medroxyprogesterone acetate)), and corticosteroids (prednisone, dexamethasone, hydrocortisone).

Examples of immunological adjuvants that can be associated with the matrix include, but are not limited, to, TLR ligands, C-Type Lectin Receptor ligands, NOD-Like Receptor ligands, RLR ligands, and RAGE ligands. TLR ligands can include lipopolysaccharide (LPS) and derivatives thereof, as well as lipid A and derivatives there of including, but not limited to, monophosphoryl lipid A (MPL), glycopyranosyl lipid A, PET-lipid A, and 3-O-desacyl-4'-monophosphoryl lipid A. In a specific embodiment, the immunological adjuvant is NPL. In another embodiment, the immunological adjuvant is LPS. TLR ligands can also include, but not limited to, TLR3 ligands (e.g., polyinosinic-polycytidylic acid (poly(I:C)), TLR7 ligands (e.g., imiquimod and resiquimod), and TLR9 ligands.

The matrix may also include antigens and/or adjuvants (i.e., molecules enhancing an immune response). Peptide, protein, and DNA based vaccines may be used to induce immunity to various diseases or conditions. DNA-based vaccines include two major components, DNA carriers (or delivery vehicles) and DNAs encoding antigens. DNA carriers protect DNA from degradation, and can facilitate DNA entry to specific tissues or cells and expression at an efficient level.

Preferred therapeutic proteins include Natalizumab (TYSABRI®), Cetuximab (ERBITUX®), Bevacizumab (AVASTIN®), Trastuzumab (HERCEPTIN®), Infliximab (REMICADE®), Rituximab (RITUXAN®), Panitumumab (VECTIBIX®), Ofatumumab (ARZERRA®), Tocilizumab (ACTEMRA®), Alemtuzumab (marketed under several trade names), Brodalumab (developed by Amgen), Denosumab (PROLIA® and XGEVA®), belimumab (BENLYSTA®), golimumab (SIMPONI ARIA®), abciximab (REOPRO®), the combination of tositumomab and iodine-131 tositumomab marketed as BEXXAR®, alemtuzumab (CAMPATH®), palivizumab (SYNAGIS®), panitumumab (VECTIBIX®), ofatumumab (ARZERRA®), basiliximab (SIMULECT®), ado-trastuzumab emtansine (KADCYLA®), Pertuzumab (PERJETA®), capromab pendetide (PROSTASCINT KIT®), daclizumab (ZENAPAX®), ibritumomab tiuxetan (ZEVALIN®), eculizumab (SOLIRIS®), tocilizumab (ACTEMRA®), rituximab (RITUXAN®), ipilimumab (YERVOY®), muromonab-CD3 (ORTHOCLONE OKT3®), raxibacumab, nimotuzumab (THERACIM®), brentuximab vedotin (ADCETRIS®), asparaginase *Erwinia chrysanthemi* (ERWINAZE®), incobotulinumtoxin A (XEOMIN®), pegloticase (KRYSTEXXA®), abobotulinumtoxin A (DYSPORT®), Alglucosidase alfa (LUMIZYME®), Ziv-aflibercept (ZAL-TRAP®), Alteplase (ACTIVASE®), Glucarpidase (VO-RAXAZE®), vedolizumab, ramucirumab, obinutuzumab, moxetumomab pasudotox, tildrakizumab, rilotumumab, AMG 145, elotuzumab, epratuzumab, farletuzumab, gantenerumab, gevokizumab, inotuzumab ozogamicin, itolizumab, ixekizumab, lebrikizumab, mepolizumab, naptumomab estafenatox, necitumumab, nivolumab, obinutuzumab, ocrelizumab, onartuzumab, racotumomab, ramucirumab, reslizumab, romosozumab, sarilumab, secukinumab, sirukumab, solanezumab, tabalumab, vedolizumab, trastuzumab emtansine (KADCYLA®), MABp1, Evolocumab, Certolizumab pegol (CIMZIA®), Clazakizumab, CNTO-136 (sirukumab), CNTO-1959, Canakinumab, Mavrilimumab, Olokizumab, Ozoralizumab, Rontalizumab Sifalimumab, ferroportin, hepcidin mAb, enavatuzumab, volociximab, ENBREL® (Etanercept), HUMIRA® (Adalimumab), SIMPONI® (Golimumab), SYNAGIS® (Palivizumab), EPOGEN® (Epoetin Alfa), PROCRIT® (Epoetin Alfa), ARANESP®, (darbepoetin alfa), ORENCIA® (Abatacept), BATASERON® (interferon beta-1b), XOLAIR® (omalizumab), STELERA® (Ustekinumab), Evolocumab, Brodalumab, Romosozumab, Denosumab, Sirukumab, Daclizumab, Alemtuzumab, Sarilumab, Alirocumab, Bococizumab, Tanezumab, Tildrakizumab, Lebrikizumab and Gantenerumab, Alglucosidase alfa (LUMIZYME®), Pegdamase bovine (ADAGEN®), α-Galactosidase, Agalsidase alfa (REPLAGAL®) Agalsidase beta (FABRAZYME®), Rasburicase (ELITEK®), Imiglucerase (CEREZYME®), Taliglucerase alfa (ELEYSO®), Laronidase (ALDURAZYME®), Elosufase alfa (VIMIZIM®), Vibriolysin, certolizumab pegol (CIMZIA®), Naglazume (Galsulfase); Elaprase (Idursulfase); Myozyme (alglucosidase alfa); VPRIV (velaglucerase) BMN-190; BMN-250; Lamazyme; Galazyme; ZA-011; Sebelipase alfa; SBC-103; HGT-1110; Replagal, Migalastat, Alzumab, Vectibix, Arzerra, Kadeyla, Perjeta, BIOMAB EGFR, Adcetris, Gazyva, Campath, Simulect, Zenapax, Zevalin, Yervoy, Orthoclone OKT3, Raxibacumab, Krystexxa, Bexxar, Soliris, Vedolizumab, Ramucirumab, XilonixMABp1, Epratuzumab, Farletuzumab, Necitumumab, Nivolumab, Obinutuzumab, Ocrelizumab, Onartuzumab, Rarnuctrumab, Reslizumab, Solanezumab, Vedolizumab, Alprolix/rFIXFc, Eloctate/rFVIIIFc, GA101, Inotuzumab Ozogamicin, Daratumumab, Siltuximab, Elotuzumab, ALX-0061, ALX-0962, ALX-0761, BI 1034020, Bimagumab (BYM338), CT-011, actoxumab/bezlotoxumab (MK-3515A), MK-3475, Dalotuzumab, AMG 139, AMG 557, AMG 729, AMG 157, AMG 780, AMG 820, AMG 811, BIIB033, AGS-009, Epratuzumab, MEDI-546, MEDI-551, PD0360324, PF05280586, SAR156597, SAR339658, Dupilumab, SAR256212, SAR279356, SAR3419, SAR153192 (enoticumab), SAR650984, SAR566658, SAR307746 (Nesvacumab), SAR391786, SAR228810, SAR252067, SAR113244, Sifalimumab, 8H9, ch14.18, ABT-806, Enavatuzumab, Volociximab (M200), Actimab-A (M195), Iomab-B, ASG-5ME, ASG-22ME, Voretuzumab mafodotin, ALT-836, DEDN6526A, DFRF4539A, MINT1526A, BMS-982470, Lirilumab, Urelumab, APN301, AV-203, BAY 79-4620, BAY 20-10112, BHQ880, 212-PbTCMtrastuzumab, AbGn-7, SGN-CD19A, SGN-CD33A, SGN-LIV1A, ASG 15ME, AntiLingo, B11B037, AntiTWEAK, ALXN1007, Teprotumumab, Artrukinzumab (IMA-638), PF-05285401, Ponezumab (PF-04360365), PF-03446962, PF-05231023, RN317 (PP-05335810), Dekavil, PP-06342674, PP-05236812 (AAB-003), PF-05082566, PF-06263507, PF-05230907, PF05280602, PF06252616, RG7116, RG7155, RG7212, RG7221, RG7356, RG7446, RG7450, RG7458, RG7598, RG7599, RG7600, RG7636, RG7842, RG7446, RG7593, RG7596, RG7597, RG7686, RG7624d, CHU, Etrolizumab, quilizumab, ranibizumab, lampalizumab, inclacumab, RG7652, Gentenerumab, crenezumab, HuMaxTFADC, MOR103, BT061, MOR208, OMP59R5, VAY736, MOR202, BAY94/9343, LJM716, Vantictumab, Demcizumab, OMP52M51, OMP54F28, Ozanezumab, Mapatumumab, GSK933776, GSK249320, GSK1070806, GSK1995057, NN8828, Concizumab, NN8210, NN8765, MEDI4893, MEDI573, Tremelimumab, MEDI0639, MEDI3617, MED14736, MEDI6469, MEDI0680, MEDI2070, MEDI5872, Tralokinumab, XmAb5871, XmAb7195, BAY1179470, CEP-37250/KHK2804, Cixutumumab, IMC-3G3, IMC-18F1; Icrucumab IMC-RON8; Namatumab, IMC-35C, IMC-20D7S, AGS-16M8F AGS-16C3F, LY2541546, Cixutumumab, LY3016859, LY2495655, Olaratumab (LY3012207LY2875358, LY2812176, Irucumab (IMC-18F1), Veltuzumab, Fulranumab, namilumab, VRS-317 GH-XTEN; Factor VIIa, Factor VIII, Factor IX; VERS-859 Extendin4-XTEN; AMX-256 GLP2-2GXTEN; AMX-179 Golate-XTREN-DM1.

Particularly preferred proteins include PDGF, SDF-1, VEGF, insulin, GM-CSF, IL-12, IL-10, GLP-1, IL-6R, IL-17, TNF-α, and TGF-β1.

In certain embodiments, the bioactive agent is an agent for the treatment of Crohn's disease. Exemplary agents include, but are not limited to, infliximab, adalimumab, certolizumab, natalizumab, vedolizumab, J695, golimumab, CDP-870, AMG-181, and ustekinumab.

In other embodiments, the therapeutic agent is a small molecule. Exemplary small molecules include, but are not limited to, steroids, anthracyclines such as doxorubicin and daunorubicin, sulfasalazine, griseofulvin and related compounds such as griseoverdin; some anti-malaria drugs (e.g. Atovaquone); immune system modulators (e.g. cyclosporine); and cardiovascular drugs (e.g. digoxin and spironolactone); and ibuprofen (analgesic); ritonavir, nevirapine, lopinavir (antiviral); clofazinine (leprostatic); diloxanide furoate (anti-amebic); glibenclamide (anti-diabetes); nifedipine (anti-anginal); spironolactone (diuretic); steroidal drugs such as danazol; carbamazepine, and anti-virals such as acyclovir. Other small molecules include acetazolamide, allopurinol, dapsone, doxycycline, paracetamol, nalidixic acid, clorothiazide, tobramycin, cyclosporin, tacrolimus, and paclitaxel.

1. Size of Bioactive Agent Particles

Bioactive agent particles generally have an average particle size of between 10 nm and 5 μm. Generally, the bioactive agent particles have an average particle size of between 10 nm and 1 micron, preferably between about 100 nm and about 1 micron, more preferably between about 200 nm and about 1 micron. In certain embodiments, the bioactive agent particles are nanoparticles having a diameter of between 500 and 700 nm.

The bioactive agent particle in the compositions may be a monodisperse or polydisperse population of particles. "Monodisperse" describes a population of nanoparticles or microparticles where all of the particles are the same or nearly the same size. As used herein, a monodisperse distribution refers to particle distributions in which at least 90% of the distribution lies within 5% of the median particle size. Polydisperse populations have greater variety in the size distribution of the particles compared to monodisperse populations.

C. Other Agents

Additional agents may also be incorporated into the matrix. Such agents include chromophores, dyes, colorants, lakes, and combinations thereof.

A "chromophore" is broadly defined herein as a substance (solid, liquid, or gas) that has color or imparts a color to the nanoparticles (including when the substance itself lacks color, for example, a clear gas, but scatters electromagnetic waves, for example, light, and thus may appear colored, for example, white, blue, green, or yellow, depending on its scattering properties) under some conditions, for example, all of the time or after exposure to a certain wavelength (such as in a fluorescent substance). For example, a chromophore can be a fluorescent, phosphorescent, wavelength up-converting, or other substance that may normally be substantially invisible, but that emits ultraviolet, visible, or infrared wavelengths during and/or after exposure to wavelengths from a particular region of the electromagnetic spectrum. A chromophore can also be a substance that reversibly or irreversibly changes color spontaneously or in response to any stimulus or photobleaches when exposed to a specific light energy. For example, a chromophore can be a substance that changes appearance or photobleaches upon simultaneous absorption of multiple photons (for example two photon absorption).

As used herein, a substance (such as a chromophore) is "invisible" when essentially no color can be detected (such as in a tissue marking site) apart from the normal coloration of the substance's surroundings (such as skin or other tissue) by the naked eye under normal lighting conditions, for example, diffuse sunlight or standard artificial lighting. A substance is "undetectable" when it is invisible to the naked eye under normal lighting conditions, and also invisible by the naked eye, or a device, under any other lighting conditions (such as fluorescent, UV, or near-infrared).

The dyes can be fluorescent, chemiluminescent, reflective, in the form of amorphous, crystalline, spherical or reflective particles, or may be colorless until activated. The chromophore can be or include rifampin, beta-carotene, tetracycline, indocyanine green, Evan's blue, methylene blue, FD&C Blue No. 1 (Brilliant Blue FCF), FD&C Green No. 3 (Fast Green FCF), FD&C Red No. 3 (Erythrosine), FD&C Red No. 40, FD&C Yellow No. 5 (Tartrazine), FD&C Yellow No. 6 (Sunset Yellow FCF) or other FD&C and D&C dyes and lakes. A lake is a straight color extended on a substratum by adsorption, coprecipitation, or chemical combination that does not include any combination of ingredients made by simple mixing process. The substratum can be alumina, blanc fixe, gloss white, clay, titanium dioxide, zinc oxide, talc, rosin, aluminum benzoate, calcium carbonate, or any combination of two or more of these. The lakes are also salts prepared from one of the straight colors by combining the color with the basic radical sodium, potassium, aluminum, barium, calcium, strontium, or zirconium. In addition, chromophores include natural pigments, metal oxides (such as synthetic iron oxides and titanium dioxide) and carbon. The chromophore can be any colored substance approved by the United States Food and Drug Administration for use in humans. In certain embodiments, the chromophore can be detected by the naked eye under normal lighting conditions or when exposed to UV, near-UV, IR, or near-IR radiation.

Other dyes that can be incorporated into polymer include acid fuchsin, alcian blue, alizarin red s, auramine o, azure a and b, Bismarck brown y, brilliant cresyl blue ald, brilliant green, carmine, cibacron blue 3GA, conga red, cresyl violet acetate, crystal violet, eosin b, eosin y, erythrosin b, fast green fcf, giemsa, hematoylin, indigo carmine, Janus green b, Jenner's stain, malachite green oxalate, methyl blue, methylene blue, methyl green, methyl violet 2b, neutral red, Nile blue a, orange H, orange G, orcein, paraosaniline chloride, phloxine b, pyronin b and y, reactive blue 4 and 72, reactive brown 10, reactive green 5 and 19, reactive red 120, reactive yellow 2, 3, 13 and 86, rose bengal, safranin o, Sudan III and IV, Sudan black B anrid toluidine blue. Examples demonstrate incorporation of water-soluble dyes indigo, indocyanin green, brilliant blue G, and beta-carotene, as well as water-insoluble dye, copper-phthalocyanin.

D. Additional Polymers

The compositions can also include one or more additional polymers. The one or more additional polymers may be used to encapsulate, coat or otherwise associate with the bioactive agent prior to incorporation into the matrix. Alternatively or additionally, the one or more additional polymers may be used to encapsulate, coat or otherwise associate with the matrix after the bioactive drug has been entrapped therein. In certain cases, the bioactive agent may be encapsulated, coated or otherwise associated with one or more polymers, entrapped with the matrix, and the entrapped matrix may then be encapsulated, coated or otherwise associated with one or more polymers, which may be the same or different from the polymers associated with the bioactive agent.

One or more additional polymers may be amorphous polymers.

The additional polymer or polymers may be biodegradable or non-biodegradable, and are optionally bioadhesive. The additional polymer may be both biodegradable and bioadhesive.

In certain embodiments, the compositions include at least one additional polymer. The additional polymer allows for systemic administration of the therapeutic agent. Preferably the additional polymer is a bioadhesive polymer, more preferably polylactic acid, polyglycolic acid, poly(lactide co-glycolide), poly(fumaric-co-sebacic anhydride), blends, or copolymers thereof.

1. Bioadhesive Polymers

Suitable bioadhesive polymers are described for example in U.S. Pat. No. 6,235,313 to Mathiowitz et al., the teachings of which are incorporated herein by reference, and include polyhydroxy acids, such as poly(lactic acid), polystyrene, polyhyaluronic acids, casein, gelatin, glutin, polyanhydrides, polyacrylic acid, alginate, chitosan; polyacrylates, such as poly(methyl methacrylates), poly(ethyl methacrylates), poly butylmethacrylate), poly(isobutylmethacrylate), poly(hexlmethacrylate), poly(isodecl methacrylate), poly (lauryl methacrylate), poly(phenyl methacrylate), poly(methyl acrylate), poly(isopropyl acrylate), poly(isobutyl acrylate), and poly(octadecl acrylate); polyacrylamides; poly (fumaric-co-sebacic) acid, poly(bis carboxy phenoxy propane-co-sebacic anhydride), polyorthoesters, and copolymers, blends and mixtures thereof.

2. Bioerodible and Bioadhesive Polymers

The use of bioadhesive polymers, bioerodible polymers and bioadhesive, bioerodible polymers permits further refinement of the agent delivery. Suitable polymers include bioerodible hydrogels, such as those described by Sawhney, et al., in *Macromolecules,* 1993, 26:581-587, the teachings of which are incorporated herein by reference. Representative bioadhesive polymers include, but are not limited to, poly(ethylene-co-maleic anhydride), poly(ethylene maleic anhydride-co-L-dopamine), poly(ethylene maleic anhydride-co-phenylalanine), poly(ethylene maleic anhydride-co-tyrosine), poly(butadiene-co-maleic anhydride), poly(butadiene maleic anhydride-co-L-dopamine) (pBMAD), poly (butadiene maleic anhydride-co-phenylalanine) and poly (butadiene maleic anhydride-co-tyrosine). Representative bioerodible polymers include, but are not limited to, synthetic polymers such as poly hydroxy acids, such as polymers of lactic acid and glycolic acid, polyanhydrides, poly (ortho)esters, polyesters, polyurethanes, poly(butic acid), poly(valeric acid), poly(caprolactone), poly(hydroxybutyrate), poly(lactide-co-glycolide), poly(lactide-co-caprolactone), poly(ethylene-co-maleic anhydride), poly(ethylene maleic anhydride-co-L-dopamine), poly(ethylene maleic anhydride-co-phenylalanine), poly(ethylene maleic anhydride-co-tyrosine), poly(butadiene-co-maleic anhydride), poly(butadiene maleic anhydride-co-L-dopamine) (pB-MAD), poly(butadiene maleic anhydride-co-phenylalanine), poly(butadiene maleic anhydride-co-tyrosine), as well as blends comprising these polymers; and copolymers comprising the monomers of these polymers, and natural polymers such as alginate and other polysaccharides, collagen, chemical derivatives thereof (substitutions, additions of chemical groups, for example, alkyl, alkylene, hydroxylations, oxidations, and other modifications routinely made by those skilled in the art), albumin and other hydrophilic, proteins, zein and other prolamines and hydrophobic proteins, copolymers, blends and mixtures thereof. In general, these materials degrade either by enzymatic hydrolysis or exposure to water in vivo, by surface or bulk erosion. Representative bioerodible, bioadhesive polymers include, but are not limited to, poly(fumaric-co-sebacic)anhydride (P(FA:SA)) and poly(bis carboxy phenoxy propane-co-anhydride) (20:80) (poly (CCP:SA)).

E. Pharmaceutically Acceptable Carriers

The compositions may also include one or more pharmaceutically acceptable carriers, excipients or diluents. The pharmaceutical formulations may be produced using standard procedures. Pharmaceutically carriers, excipients or diluents for different dosage forms are known in the art, and described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, P A: Williams and Wilkins, 1995).

1. Different Types of Excipients

Typical classes of carriers, excipients and/or diluents include, but are not limited to, buffers, surfactants, preservatives, binders, lubricants, disintegrators, swelling agents, fillers, stabilizers, and combinations thereof. The term "pharmaceutically acceptable excipient" also includes all components of any coating formed around the matrix and/or bioactive agent particles, which may include plasticizers, pigments, colorants, stabilizing agents, and glidants.

Excipients may also be included, in the composition to alter its porosity and permeability. Suitable excipients may include inorganic and organic materials such as sucrose, hydroxypropyl cellulose, sodium chloride, sodium chloride, xylitol, sorbitol, lactose, dextrose, maltodextrins, and dextrates.

Excipients may also be included in the composition to alter its hydration and disintegration properties. Suitable pH dependent enteric excipients may include cellulose acetate phthalate.

Excipients may also be added as a "wicking agent" to regulate the hydration of the composition. Suitable excipients may include acdisol, hydroxypropyl cellulose, hydroxypropyl methyl cellulose, cellulose acetate phthalate.

p(AA) prevents coalescence of drug domains within a spray-dried product resulting in increased drug surface area available for dissolution. Additionally, adipic acid monomer generated during polymer degradation increases acidity in the microenvironment of a spray-dried drug particle. By changing the pH, some of the drugs may become more soluble.

a. Coating Materials

The composition may further be coated with a polymer to facilitate oral administration, and to protect the bioactive agent from acidic environments, such as found in the stomach. Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, methacrylic resins, zein, shellac, and polysaccharides.

Additionally, the coating material may contain conventional carriers such as plasticizers, pigments, colorants, glidants, stabilization agents, pore formers and surfactants.

b. Surfactants

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, Pluronics, stearoyl monoisopropanolamide, and polyoxyethylene hydrogenated tallow amide. Examples of amphoteric surfactants include sodium N-dodecyl-.beta.-alanine, sodium N-lauryl-β-iminodipropionate, myristoamphoacetate, lauryl betaine lauryl sulfobetaine, and lecithin.

2. Liquid or Injectable Drug Delivery Dosage Forms

Preferably the matrices are in the form of a plurality of particles, which are dispersed or suspended in a pharmaceutically acceptable carrier, such as a diluent. Generally the plurality of particles is dispersed or suspended in the carrier immediately before it is administered. Suitable diluents include an appropriate buffer, for example, phosphate buffered saline or other physiologically compatible solutions. Surfactant such as TWEEN™, or polyethylene glycol, sodium lauryl sulfate, sodium caprate, pluronics, Span 80 and lecithin may be incorporated into the suspension or dispersion as needed.

3. Solid Drug Delivery Dosage Forms

Optionally, the matrices are further formulated into solid drug delivery dosage forms, such as tablets, capsules, multiparticulates, beads, or granules. The solid dosage forms may be prepared by conventional means with pharmaceutically acceptable excipients such as binding agents (e.g., acacia, methylcellulose, sodium carboxymethylcellulose, polyvinylpyrrolidone (Povidone), hydroxypropyl methylcellulose (HPMC), sucrose, starch, and ethylcellulose); fillers (e.g., corn starch, gelatin, lactose, acacia, sucrose, microcrystalline cellulose, kaolin, mannitol, dicalcium phosphate, calcium carbonate, sodium chloride, or alginic acid); lubricants (e.g. magnesium stearates, stearic acid, silicone fluid, talc, waxes, oils, and colloidal silica); and disintegrators (e.g. micro-crystalline cellulose, corn starch, sodium starch glycolate and alginic acid. Optional pharmaceutically acceptable excipients present in the tablets, multiparticulate formulations, beads, granules, or particles include, but are not limited to, diluents, binders, lubricants, disintegrants, colorants, stabilizers, and surfactants.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet, multiparticulate, bead, or granule remains intact during storage and until administration. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

If desired, the tablets, beads, granules, or particles may also contain minor amounts of nontoxic auxiliary substances, such as wetting or emulsifying agents, dyes, pH buffering agents, and/or preservatives.

Bioactive agents exhibit increased storage stability when incorporated into the matrix. After storage at 4° C. for 32 weeks, the release from the particles of the bioactive agent into an aqueous solution is at least 30, 35, 40, 45, 50, 55, 60, 65, 70, 75, 80, 85, 90, or 95% of the amount of bioactive agent released from a fleshly prepared matrix. Similarly, after storage at 4° C. for 32 weeks, the bioactivity of the active agent released from the particles is at least 30, 35, 40, 45, 50, 55, 60, 65, 70, 75, 80, 85, 90, or 95% the bioactivity of bioactive agent released from a freshly prepared matrix.

III. Methods of Making

A. Methods of Micronizing Bioactive Agents

The bioactive agent may be micronized prior to incorporation into the matrix to form microparticles or nanoparticles of agent.

Optionally, the micro- or nanoparticles containing the bioactive agent include one or more biocompatible polymers, such as the biocompatible polymers described above. The identity and quantity of the one or more additional polymers can be selected, for example, to influence particle stability, i.e. that time required for distribution to the site where delivery is desired, and the time desired for delivery. Pharmaceutically acceptable excipients, including pH modifying agents, disintegrants, preservatives, and antioxidants, can be incorporated during micro- and nanoparticle formation.

Common microencapsulation techniques include, but are not limited to, spray drying, interfacial polymerization, hot melt encapsulation, phase separation encapsulation (spontaneous emulsion microencapsulation, solvent evaporation microencapsulation, and solvent removal microencapsulation), coacervation, low temperature microsphere formation, and phase inversion nanoencapsulation (PIN).

Exemplary methods of micro- and nanoparticle formulation are briefly described below.

1. Spray Drying

Spray drying could be used to make micronized proteins as well as encapsulated proteins after micronization. Methods for forming encapsulated microspheres/nanospheres using spray drying techniques are described in U.S. Pat. No. 6,620,617, to Mathiowitz et al. In this method, the polymer, optionally with one or more excipients, is dissolved in an organic solvent such as methylene chloride or in water. Alternative solvent systems are known, and include a mixture of water and tert-butyl alcohol (TBA). A known amount of one or more active agents to be incorporated in the particles is suspended (in the case of an insoluble active agent) or co-dissolved (in the case of a soluble active agent) in the polymer solution. Preferably, the active agent and the polymer dissolve in the solvent system.

The solution or dispersion is pumped through a micronizing nozzle driven by a flow of compressed gas, and the resulting aerosol is suspended in a heated cyclone of air, allowing the solvent to evaporate from the microdroplets, forming particles. Microspheres/nanospheres ranging between 0.1-10 microns can be obtained using this method. Preferably the particles formed by this spray drying step range from about 1 to about 10 µm in size 2. Hot Melt Microencapsulation Microspheres can be formed from polymers such as polyesters and polyanhydrides using hot melt microencapsulation methods as described in Mathiowitz et al., *Reactive Polymers*, 6:275 (1987). In this method, the use of polymers with molecular weights between 3-75,000 daltons is preferred. In this method, the polymer first is melted and then mixed with the solid particles of one or more active agents to be incorporated that have been sieved to less than 50 microns. The mixture is suspended in a non-miscible solvent (like silicon oil), and, with continuous stirring, heated to 5° C. above the melting point of the polymer. Once the emulsion is stabilized, it is cooled until the polymer particles solidify. The resulting microspheres are washed by decanting with petroleum ether to give a free-flowing powder.

3. Phase Separation Microencapsulation

In phase separation microencapsulation techniques, a polymer solution is stirred, optionally in the presence of one or more active agents to be encapsulated. While continuing to uniformly suspend the material through stirring, a non-solvent for the polymer is slowly added to the solution to decrease the polymer's solubility. Depending on the solubility of the polymer in the solvent and nonsolvent, the polymer either precipitates or phase separates into a polymer rich and a polymer poor phase. Under proper conditions, the polymer in the polymer rich phase will migrate to the interface with the continuous phase, encapsulating the active agent(s) in a droplet with an outer polymer shell.

a. Spontaneous Emulsion Microencapsulation

Spontaneous emulsification involves solidifying emulsified liquid polymer droplets formed above by changing temperature, evaporating solvent, or adding chemical cross-linking agents. The physical and chemical properties of the encapsulant, as well as the properties of the one or more active agents optionally incorporated into the nascent particles, dictates suitable methods of encapsulation. Factors such as hydrophobicity, molecular weight, chemical stability, and thermal stability affect encapsulation.

b. Solvent Evaporation Microencapsulation

Methods for forming microspheres using solvent evaporation techniques are described in E. Mathiowitz et al., *J. Scanning Microscopy*, 4:329 (1990); L. R. Beck et al. *Fertil. Steril.*, 31:545 (1979); L. R. Beck et al *Am J Obstet Gynecol* 135(3) (1979); S. Benita et al., *J. Pharm. Sci.*, 73:1721 (1984); and U.S. Pat. No. 3,960,757 to Morishita et al. The polymer is dissolved in a volatile organic solvent, such as methylene chloride. One or more active agents to be incorporated are optionally added to the solution, and the mixture is suspended in an aqueous solution that contains a surface active agent such as poly(vinyl alcohol). The resulting emulsion is stirred until most of the organic solvent evaporated, leaving solid microspheres/nanospheres. This method is useful for relatively stable polymers like polyesters and polystyrene. However, labile polymers, such as polyanhydrides, may degrade during the fabrication process due to the presence of water. For these polymers, some of the following methods performed in completely anhydrous organic solvents are more useful.

c. Solvent Removal Microencapsulation

The solvent removal microencapsulation technique is primarily designed for polyanhydrides and is described, for example, in WO 93/21906 to Brown University Research Foundation. In this method, the substance to be incorporated is dispersed or dissolved in a solution of the selected polymer in a volatile organic solvent, such as methylene chloride. This mixture is suspended by stirring in an organic oil, such as silicon oil, to form an emulsion. Microspheres that range between 1-300 microns can be obtained by this procedure. Substances which can be incorporated in the microspheres include pharmaceuticals, pesticides, nutrients, imaging agents, and metal compounds.

4. Coacervation

Encapsulation procedures for various substances using coacervation techniques are known in the art, for example, in GB-B-929 406; GB-B-929 40 1; and U.S. Pat. Nos. 3,266,987, 4,794,000, and 4,460,563. Coacervation involves the separation of a macromolecular solution into two immiscible liquid phases. One phase is a dense coacervate phase, which contains a high concentration of the polymer encapsulant (and optionally one or more active agents), while the second phase contains a low concentration of the polymer. Within the dense coacervate phase, the polymer encapsulant forms nanoscale or microscale droplets. Coacervation may be induced by a temperature change, addition of a non-solvent or addition of a micro-salt (simple coacervation), or by the addition of another polymer thereby forming an interpolymer complex (complex coacervation).

5. Low Temperature Casting of Microspheres

Methods for very low temperature casting of controlled release microspheres are described in U.S. Pat. No. 5,019,400 to Gombotz et al. In this method, a polymer is dissolved in a solvent optionally with one or more dissolved or dispersed active agents. The mixture is then atomized into a vessel containing a liquid non-solvent at a temperature below the freezing point of the polymer-substance solution which freezes the polymer droplets. As the droplets and non-solvent for the polymer are warmed, the solvent in the droplets thaws and is extracted into the non-solvent, resulting in the hardening of the microspheres.

6. Phase Inversion Nanoencapsulation (PIA)

Nanoparticles can also be formed using the phase inversion nanoencapsulation (PIN) method, wherein a polymer is dissolved in a "good" solvent, fine particles of a substance to be incorporated, such as a drug, are mixed or dissolved in the polymer solution, and the mixture is poured into a strong non-solvent for the polymer, to spontaneously produce, under favorable conditions, polymeric microspheres, wherein the polymer is either coated with the particles or the particles are dispersed in the polymer. See, e.g., U.S. Pat. No. 6,143.211 to Mathiowitz, et al. The method can be used to produce monodisperse populations of nanoparticles and microparticles in a wide range of sizes, including, for example, about 100 nanometers to about 10 microns.

Advantageously, an emulsion need not be formed prior to precipitation. The process can be used to form microspheres from thermoplastic polymers.

7. Sequential Phase Inversion Nanoencapsulation (sPIN)

Multi-walled nanoparticles can also be formed by a process referred to as "sequential phase inversion nanoencapsulation" (sPIN), which is described in U.S. Pat. No. 8,673,359 to Cho, et al. sPIN is particularly suited for forming monodisperse populations of nanoparticles, avoiding the need for an additional separations step to achieve a monodisperse population of nanoparticles.

B. Methods of Preparing the Matrix

The matrix is prepared by dissolving the semi-crystalline water soluble polymer in a suitable solvent. Additional biocompatible polymers may be added to the solution as well. Suitable solvents are polar organic solvents, and include dichloromethane, ethanol, THF, propanol, DMSO, acetone, acetonitrile, ethyl acetate, nitromethane, methanol and mixtures thereof. A preferred solvent is dichloromethane, either alone or in combination with an aliphatic alcohol such as ethanol or methanol. A combination of dichloromethane and ethanol is especially preferred. This solution is then combined with the therapeutic agent, which may have been micronized or encapsulated, preferably according to one of the techniques described above.

The polymer solution is sufficiently concentrated so that the therapeutic agent does not dissolve.

The solvent is then removed from the turbid mixture in a manner sufficient to form the crystalline matrix. The solvent may be removed in any method suitable for forming particles, such as those described above with respect to micronization. Generally, methods which remove the solvent slowly are preferred over those which cause a fast precipitation of the particles and polymers. Such methods include, but are not limited to, spray drying, film casting, pan coating in a fluidized bed reactor, lyophilizing, rotary evaporation, and solvent casting.

Additionally, the combination of the turbid mixture with an anti-solvent, which produces a rapid precipitation, is also suitable for embedding the particles into the matrix. Preferred anti-solvents include, but are not limited to, hydrocarbons such as pentanes, hexanes, heptanes, petroleum ethers, and ligroin.

In a preferred embodiment, a therapeutic agent is micronized using a spray drying process. For example, a protein, such as TGFβ1, and at least one polyethylene glycol, such as PEG 3350 and/or PEG 4500, and at least one poloxamer, such as PLURONIC® F127, may be mixed with or without excipients, in a suitable solvent system to dissolve the agent, polymer(s), and excipients, such as tert-butyl alcohol in water. Then the mixture can be atomized at a suitable liquid feed rate, pressure, inlet and outlet temperature, and drying gas flow rate to form micronized particles of agent.

In a further preferred embodiment, the micronized agent is incorporated into a matrix using a spray drying process. For example, a therapeutic agent, preferably in the form of microparticles or nanoparticles, is mixed with one or more semi-crystalline, water soluble matrix forming polymers. The matrix forming polymers include at least one semi-crystalline polymer. Preferably a combination of two or more semi-crystalline, matrix forming polymers are present, such as a polyethylene glycol, such as PEG 3350 and/or PEG 4500, and at least one poloxamer, such as PLURONIC® F127. Additionally, the feedstock may contain amorphous polymers, such as PLA and/or PLGA. The feedstock may contain additional excipients, such as surfactants (e.g. Tween 20 and Tween 80), sucrose, glycine, and PVP. The agent and water soluble semi-crystalline matrix forming polymers, optionally with additional polymers and excipients, are mixed together in a suitable solvent, such as dichloromethane (DCM), ethanol, and water, which dissolves the polymers and excipients. The agent is typically dispersed in the polymer solution (feedstock).

The feedstock is sprayed through a suitable atomizer at a suitable liquid feed rate, pressure, inlet and outlet temperature, and drying gas flow rate to form matrices containing the agent, where the semi-crystalline polymer(s) constitutes at least 30% by weight of the matrix, preferably at least 35%, 40%, or 50% by weight of the matrix, and even more preferably constitutes at least 65% by weight of the matrix.

IV. Methods of Using

The compositions can be formulated into a variety of different drug delivery dosage forms and administered to a patient by any suitable method, including oral, injection (subcutaneous, intramuscular, intravenous), sublingual, inhalation, and transdermal delivery.

The compositions can be administered as a depot to a patient. For example, the depot could be injected or implanted subcutaneously to allow for controlled delivery of a drug over a period of time, such as 1 month or longer, or up to one year or longer. In a preferred embodiment, the drug is one or more antibodies.

In one embodiment, the microparticles can be used to deliver active agents to specific areas along the gastrointestinal tract. The results in the Examples demonstrate that uptake and release of microparticles was effectively localized to the gut-associated lymphoid tissue (GALT) and the mesenteric lymph nodes (MLN).

The administration of therapeutic agents that are encapsulated prior to incorporation into the matrix permits the systemic administration of the agent via oral delivery of the agents. In cases in which the agent is not encapsulated, the agents are delivered to topical sites within the gastrointestinal tract.

In some embodiments, the microparticles release least 30% of the bioactive agent in the intestines. In other embodiments, at least 35, 40, 45, 50, 55, 60, 65, 70, 75, or 80% of the bioactive agent is released in the intestines.

In a preferred embodiment, the microparticles are used to deliver proteins and other bioactive agents to Peyer's patches and other lymphoid tissue, such as gastrointestinal enterocytes. In these embodiments, the bioactive agent can be used to treat conditions associated with Peyer's patches and other lymphoid tissue. The formulations may be administered in an effective manner and amount to treat a variety of diseases, disorders and/or conditions, such as Crohn's disease, ulcerative colitis, irritable bowel syndrome, gastrointestinal cancer, or celiac disease. Exemplary gastrointestinal cancers include gastric cancer, stromal tumors, lipomas hamartomas and carcinoid syndromes.

EXAMPLES

Example 1

Preparation of Encapsulated TGF-β1

Step 1

25 mg each of Tween® 20, Tween® 80, PEG 4500 and Pluronic F127 were added to 1 ml of doubly distilled water (solution A). 50 mg each of sucrose, glycine and PVP K15 were added to 1 ml doubly distilled water (solution B). Each solution was filtered with a sterile filter using 0.2 μm syringe into new cryotube vials. 7.2 μl of solution A and 71.7 μl of solution B were added by pipet to a lyophilization viral containing 5.0 ml of 99% tert-butyl alcohol. 500 μl of 1.00 mg/ml stock solution of mTGF-β1 (Peprotech) was added, followed by lyophilization. The mixture was lyophilized at −40° C. for 120 min.

Step 2

250 mg of low MW PLA~9 KDa and 250 mg of medium MW PLA~36 KDa polymer were dissolved in 6 ml dichloromethane. 2.25 g of PEG 3350 and 0.75 g of Pluronic F127 were added to the PLA solution and dissolved with ten seconds of vortex. 1.67 ml 97% EtOH was added to the solution containing PLA, PFG3350 and F127 and mixed thoroughly. Approximately 2.0 ml of the PLA, PEG-3350 and F127 solution was added to the vial containing the lyophilized mTGF-β1, which was bath sonicated for 30 seconds while continually swirling the vial. The mTGF-β1-containing mixture was added to the remainder of the PLA, PEG3350 and F127 solution.

Step 3

1 liter of heptane and 0.1 ml Span 80 were combined in a reactor equipped with a glass impeller. While the heptane solution was stirring, the polymer solution was added topwise using an automatic pipette. The solution was stirred for 30-45 minutes. The solution was then filtered under argon gas between 10-15 psi Ar gas using a 0.2 μm Teflon filter into a stirred cell. The reactor was washed with 300 ml of heptane to ensure complete recovery of the materials. After all the solution was filtered, argon pressure was maintained over the filter for 10-15 minutes to dry the mTGF-β1 formulation. The microspheres were collected by scraping the powder from the filter paper into a 50 ml Falcon tube. The powder was dried under vacuum overnight.

Using the protocol described above, the following proteins have also been encapsulated: GM-CSF, IL-12, IL-10, GLP-1, IL-6R, IL-17, VEGF, PDGF, and TGF-β1.

Example 2

Preparation of Blank Particles

The process described in Example 1 was used to prepare blank matrices by substituting 500 μl of doubly distilled water for the mTGF-β1 solution. The matrices were precipitated from a solution of 500 ml heptane and 0.05 ml Span 80.

Example 3

Dissolution Studies of Polymer Matrix

In order to determine the stability of various polymer excipient blends, films were casts using the polymers described below. The polymers were dissolved in dichloromethane and the clear solutions were cast into a glass petri dish. The dichloromethane was allowed to evaporate under ambient conditions to provide the film.

TABLE 1

| | Composition | Ratio (w-w) |
|---|---|---|
| #1 | 1 g PLLA, 5 g PEG 3350 | 16.7%-83.3% |
| #2 | 1 g PLGA, 5 g PEG 3350 | 16.7%-83.3% |
| #3 | 1 g FASA, 5 g PEG 3350 | 16.7%-83.3% |
| #4 | 1 g PS, 5 g PEG 3350 | 16.7%-83.3% |
| #5 | 0.5 g PLLA, 2.75 g PEG 3350 | 15.4%-84.6% |
| #6 | 0.25 g PLLA, 1.125 g PEG 3350, 0.375 g F127 | 14.3%-64.3%-21.4% |
| #7 | 0.5 g PLLA, 0.1 g PEG 3350 | 83.3%-16.7% |
| #8 | 5 g PEG 3350 | 0%-100% |

Key:
PLLA = Poly-1-lactic acid (50%/50% low/high MW)
PLGA = Polylactic co-glycolic acid (RG 503 H)
FASA = Polyfumaric-co-sebacic anhydride (20:80)
PS = Polystyrene Samples weighing approximately 37.7 mg were scraped from each of the above films. Accurate masses were obtained from each sample, and each sample was then placed in a previously weighed microcentrifuge tube. A 1 ml solution of aqueous buffer (either pH 2.0 or 7.4) was added to each tube. After either 1 or 24 hours the tubes were centrifuged, and the residue was flash frozen and lyophilized.

Results

Tables 2-5 report the residual mass of polymer after being submerged in the different buffer solutions.

TABLE 2

Dissolution Results in buffer pH 7.4, 1 hour

| | Blank Tube (mg) | Initial Polymer (mg) | Tube mass after exposure (mg) | Remaining polymer (calc.) | Remaining polymer, % (calc). |
|---|---|---|---|---|---|
| 1 | 1008.5 | 38.2 | 1019.9 | 11.4 | 29.84 |
| 2 | 1009.1 | 38.1 | 1014.9 | 5.8 | 15.22 |
| 3 | 1017.9 | 37.6 | 1042.8 | 24.9 | 66.22 |
| 4 | 1012.9 | 38.6 | 1028.8 | 15.9 | 41.19 |
| 5 | 1018.9 | 39.1 | 1031.2 | 12.3 | 31.46 |
| 6 | 1009.8 | 38.7 | 1020.9 | 11.1 | 28.68 |
| 7 | 1024.4 | 45.1 | 1068 | 43.6 | 96.67 |
| 8 | 1012.7 | 38.3 | 1013.9 | 1.2 | 3.13 |

TABLE 3

Dissolution Results in buffer pH 7.4, 24 hours

| | Blank Tube (mg) | Initial Polymer (mg) | Tube mass after exposure (mg) | Remaining polymer (calc.) | Remaining polymer, % (calc.) |
|---|---|---|---|---|---|
| 1 | 1022.4 | 37.9 | 1031.5 | 9.1 | 24.01 |
| 2 | 1021 | 37.8 | 1024.6 | 3.6 | 9.52 |
| 3 | 1013.8 | 37.5 | 1024.3 | 10.5 | 28.00 |
| 4 | 1013.9 | 37.7 | 1021.7 | 7.8 | 20.69 |
| 5 | 1017.5 | 38.3 | 1026.9 | 9.4 | 24.54 |
| 6 | 1017.4 | 38.7 | 1023.5 | 6.1 | 15.76 |
| 7 | 1017.6 | 40 | 1055.6 | 38 | 95.00 |
| 8 | 1017.5 | 33.4 | 1017.5 | 0 | 0.00 |

TABLE 4

Dissolution Results in buffer pH 2.0, 1 hour

| | Blank Tube (mg) | Initial Polymer (mg) | Tube mass after exposure (mg) | Remaining polymer (calc.) | Remaining polymer, % (calc.) |
|---|---|---|---|---|---|
| 1 | 1025.1 | 37.8 | 1034.6 | 9.5 | 25.13 |
| 2 | 1009.3 | 37.9 | 1015.5 | 6.2 | 16.36 |
| 3 | 1021.2 | 38.5 | 1033.1 | 11.9 | 30.91 |
| 4 | 1013.2 | 38.8 | 1026.8 | 13.6 | 35.05 |
| 5 | 1012.9 | 38.1 | 1023.3 | 10.4 | 27.30 |
| 6 | 1021 | 37.5 | 1028.6 | 7.6 | 20.27 |
| 7 | 1013.2 | 40.1 | 1052.4 | 39.2 | 97.76 |
| 8 | 1024.5 | 38.9 | 1025.3 | 0.8 | 2.06 |

TABLE 5

Dissolution Results in buffer pH 2.0, 24 hours

| | Blank Tube (mg) | Initial Polymer (mg) | Tube mass after exposure (mg) | Remaining polymer (calc.) | Remaining polymer, % (calc.) |
|---|---|---|---|---|---|
| 1 | 1017.7 | 38.5 | 1026.7 | 9 | 23.38 |
| 2 | 1017.4 | 37.9 | 1020.5 | 3.1 | 8.18 |
| 3 | 1017.8 | 37.6 | 1028.8 | 11 | 29.26 |
| 4 | 1013.3 | 38.2 | 1024.8 | 11.5 | 30.10 |
| 5 | 1017.5 | 38 | 1026.6 | 9.1 | 23.95 |
| 6 | 1009.3 | 38.1 | 1015.3 | 6 | 15.75 |
| 7 | 1012.9 | 48.4 | 1060 | 47.1 | 97.31 |
| 8 | 1019.6 | 36.6 | 1019.6 | 0 | 0.00 |

Notably, although formulations 1-6 all contained by weight of hydrophobic polymer, a greater percentage of the mass remained after submersion of the film in aqueous solution. The amount of hydrophobic polymer would typically be expected to remain after both the 1 hour and 24 hour time points. However, the results from the dissolution studies indicate that all polymer blends were left with excess of PEG or a blend of PEG and F127 after 1 hour in both pH 2 and pH 7.4. The same results were obtained after dissolution in 24 hours, however fewer residual excipients remained. See Tables 3 and 5.

Without being bound by theory, it is believed that these results demonstrate that the excipients are in an aggregated state, which slows the dissolution of the matrix as a whole.

Example 4

Polymer Thermal Stability

Films were cast using polymers and PEG3350 similarly above. Additionally, films were cast of the polymers not containing PEG3350. PEG3350 and Pluronic® F127 films were cast singly. A Perkin Elmer® DSC 7 was used to measure the heat of fusion for each formulation. The instrument was calibrated for melting and enthalpy using an ultra-pure indium standard (ΔH=28.45 J/g). The microsphere samples (5±2 mg) were weighed into an aluminum pan with lid using a microbalance (Perkin Elmer® AD-4 Autobalance) and placed into the instrument. The samples were held at −20° C. for one minute and then heated from −20° C. to 200° C. at a rate of 10° C./min. The samples were then cooled to −20° C. at −10° C./min before being reheated again from −20° C. to 200° C. at 10° C./min. The heat of fusion of the first and second heat was then calculated from the thermogram for each sample.

The formulations made with PEG are semi-crystalline with a $T_M$ at 60° C. and a heat of fusion of 72.8 J/g. Similarly, formulations made with F127 are semi-crystalline with melting at $T_M$ 48.6° C. and a heat of fusion of 46.6 J/g.

As shown in Table 6 below, films cast with a mixture of PEG or F127 exhibit semi-crystalline characteristics, whereas films prepared solely with PLA, PLGA or FASA do not. Thus the PLA, PLGA and pFASA polymers are amorphous.

TABLE 6

| Formulation | $T_m$ (° C.) | ΔH (J/g) |
| --- | --- | --- |
| PLLA/PEG 16.7%/83.3% | 56.878 | 59.487 |
| PLGA/PEG 16.7%/83.3% | 56.701 | 48.392 |
| FASA/PEG 16.7%/83.3% | 55.349 | 61.634 |
| PS/PEG 16.7%/83.3% | 57.704 | 41.302 |
| PCL/PEG 16.7%/83.3% | 58.301 | 65.931 |
| PLLA 100% | 48.814 | 0.902 |
| PLGA 100% | 43.372 | 0.844 |
| P(FASA) 100% | 65.308 | 12.853 |
| PS 100% (no peak present) | — | — |
| PCL 100% | 56.932 | 23.506 |
| PEG 100% | 60.94 | 72.808 |
| F127 100% | 58.64 | 46.641 |

Example 5

Stability Study

Microparticles containing either mTGF-β1 or blanks were fabricated according to Examples 1 and 2 above and stored at room temperature, 4° C., and −20° C. for 3 months. Samples were obtained at the time points listed below, and assayed by DSC.

TABLE 7

| time | Melting Temperature | | | ΔH (J/g) | | |
| --- | --- | --- | --- | --- | --- | --- |
|  | RT | 4° C. | −20° C. | RT | 4° C. | −20° C. |
| Blank Particles | | | | | | |
| 0 | 57.079 | 57.079 | 57.079 | 71.953 | 71.953 | 71.953 |
| 1 mo. | 57.069 | 57.033 | 56.666 | 47.562 | 72.309 | 65.389 |
| 2 mo. | 56.7 | 57.033 | 57.279 | 73.627 | 68.355 | 68.471 |

TABLE 7-continued

| time | Melting Temperature | | | ΔH (J/g) | | |
| --- | --- | --- | --- | --- | --- | --- |
|  | RT | 4° C. | −20° C. | RT | 4° C. | −20° C. |
| mTGF-β1 particles | | | | | | |
| 0 | 57.079 | 57.079 | 57.079 | 71.953 | 71.953 | 71.953 |
| 1 mo. | 57.069 | 57.033 | 56.666 | 47.562 | 72.309 | 65.389 |
| 2 mo. | 56.7 | 57.033 | 57.279 | 73.627 | 68.355 | 68.471 |

Figure 1:
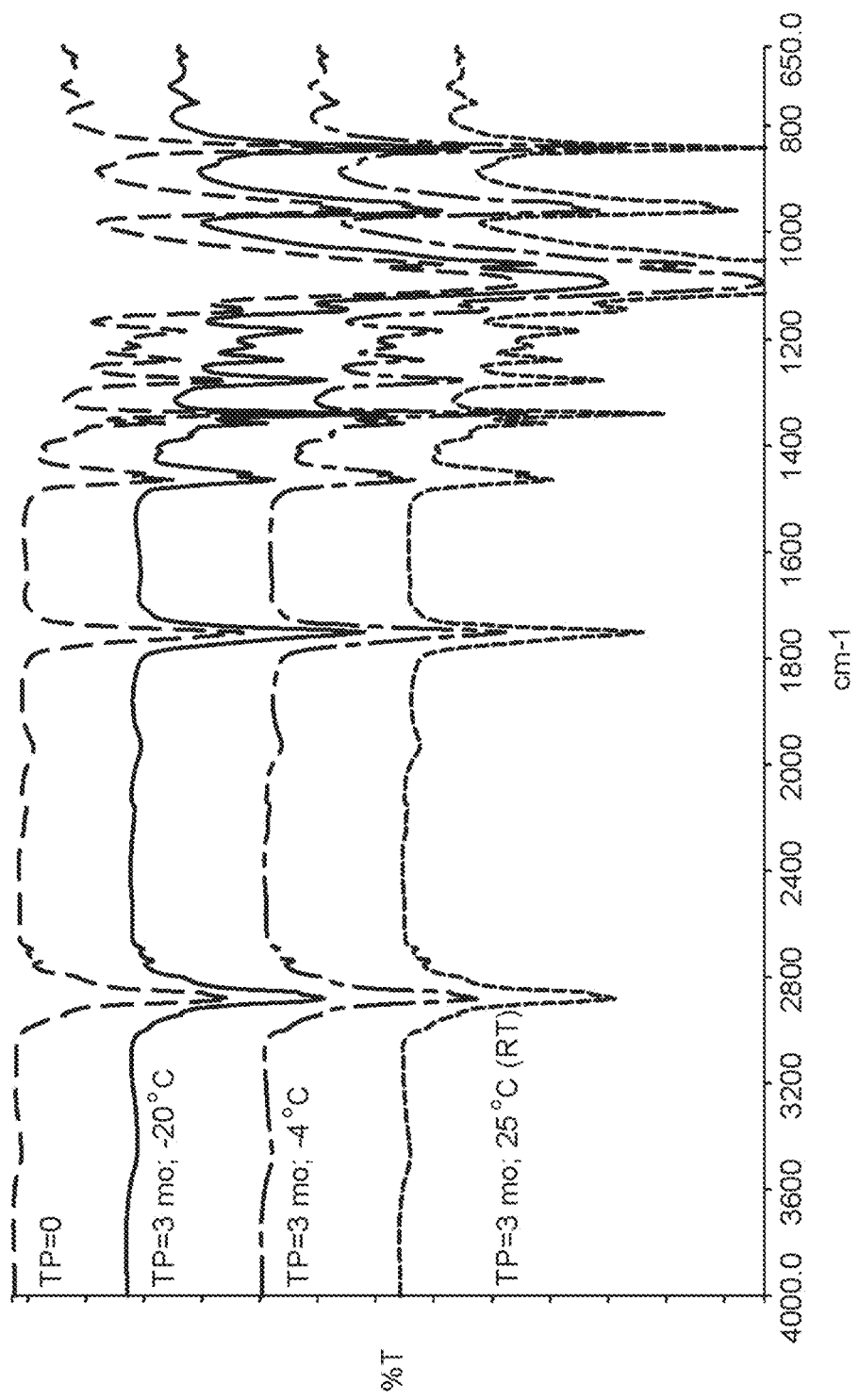
FIG. 1 depicts an overlaid IR spectrum of the blank particles at time points 0 and 3 months for each of the three storage conditions.

FIG. 1 depicts an overlaid IR spectrum of the blank particles at time points 0 and 3 months for each of the three storage conditions. The peak at approximately 1750 cm$^{-1}$, which is attributed to the PLA, did not diminish over time. This demonstrates that the PLA did not degrade.

Example 6

Storage Stability Microparticles on mTGF-β1 Release and Activity mTGF-β particles of Example 1 were stored at room temperature (RT), 4° C. and −20° C. Samples were obtained at 2, 4, 6, 8, 12, 16, 24, and 32 week time points. The in vitro release characteristics of the particles were evaluated according to the following protocol. A 10 mg sample of particles was suspended in 0.2 ml culture medium (DMEM/F12±10% FCS) and transferred to the wells of a 96-well plate in triplicate. The plate was transferred to a 37° C. 5% CO$_2$ incubator. The following day, the released sample supernatant was recovered, centrifuged to remove any remaining particles and then stored at −20° C. The biological activity of the supernatant samples was tested using the TGFβ-1 sensitive mouse lymphoblast cell line HT-2. Cells were plated in a 1.5×104 cells/well in media containing a 15 ng/ml solution of mIL-4. Standards and samples were added to the wells to produce a final volume of 200 ul/well containing 7.5 ng/ml m-IL-4 and the TGFβ-1 standard or sample as indicated. The 96 well plates were incubated 37° C., 5% CO$_2$ for 67 hours. 20 μl of Promega Cell titer 96 Aqueous One Solution Reagent was added to wells and incubated 4 hours at 37° C. and the wells were assayed by reading the optical density (OD) at 490 nm.

Figure 2A:
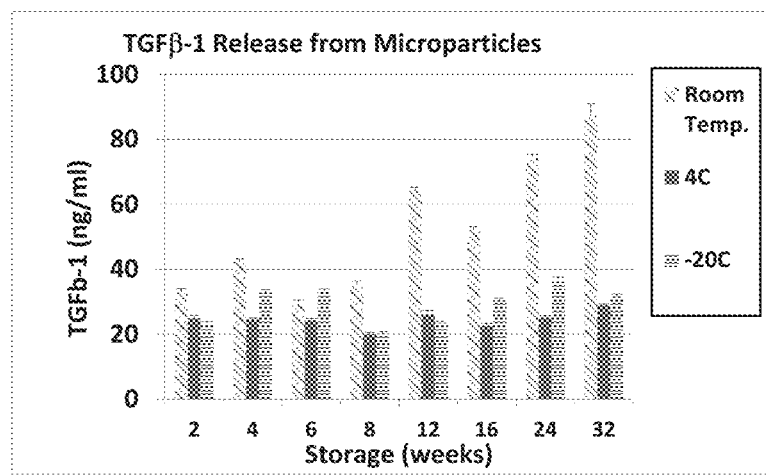
FIGS. 2A-C are bar graphs depicting the concentration of released mTGF-$\beta$1 (FIG. 2A; y-axis depicts [TGF $\beta$-1] in ng/ml), bioactivity of released mTGF-$\beta$1 (FIG. 2B; y-axis depicts relative activity), and specific activity of released mTGF-$\beta$1 (FIG. 2C; y-axis depicts specific activity of TGF $\beta$-1) from the particles stored under different conditions (room temperature (diagonal lines in bar), 4° C. (filled in bar), and −20° C. (horizontal lines in bar)) measured at different time points (x-axis; measured in weeks), relative to freshly prepared compositions containing mTGF-$\beta$1 particles.
Figure 2B:
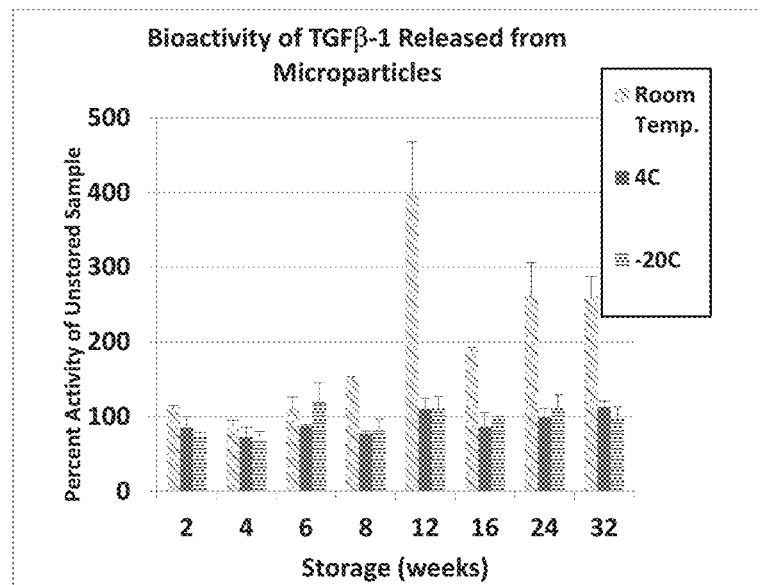
Figure 2C:
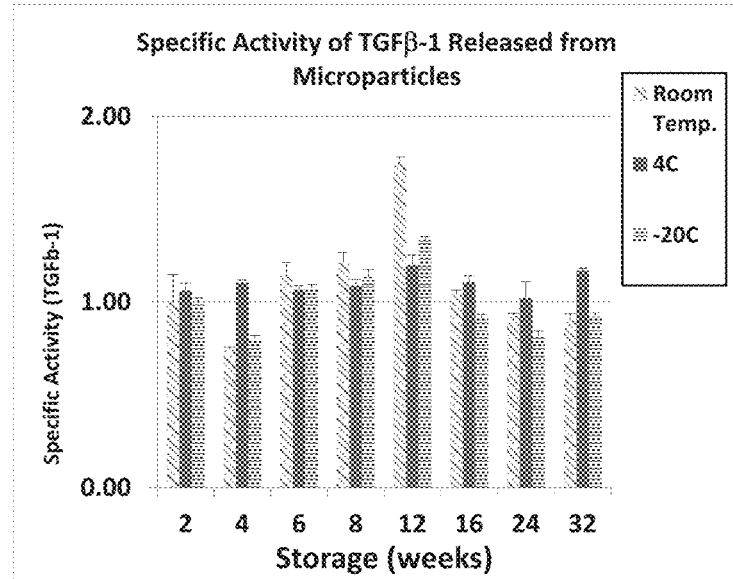

FIG. 2A depicts the concentration of mTGF-β released from the particles after storage, relative to the amount released from freshly prepared particles. FIG. 2B depicts the bioactivity of the TGF-β particles after storage, relative to the bioactivity of freshly prepared particles.

Example 7

Storage Stability of IL-12 Embedded in a Matrix

Microparticles containing IL-12 were prepared according to the process described in Example 1 and were stored at room temperature, 4° C. and −20° C. Samples were recovered at the 2, 8, 12, 16, 20, 28 and 36 week time points and used in an in vitro release assay. A 10 mg sample of particles was suspended in 0.2 ml culture medium (DMEM/F12+10% FCS) and transferred to the wells of a 96-well plate in triplicate. The plate was transferred to a 37° C. 5% CO$_2$ incubator. The following day, the released sample supernatant was recovered, centrifuged to remove any remaining particles and then frozen for storage and future use in the bioassay. The biological activity of the supernatant samples was tested in an in vitro assay using human peripheral blood lymphocytes.

Briefly, heparinized blood was obtained from healthy adult volunteers. Peripheral blood lymphocytes were isolated using centrifugation with Ficoll-Paque PLUS (Amersham Biosciences). After isolation and washing, the cells were expanded in 10 μg/ml PHAP (Phyto hemagglutinin) for three days before being frozen with DMSO and stored in liquid nitrogen.

The IL-12 microparticle release samples were diluted in DMEM/F12 tissue culture media plus 10% FCS and penicillin/streptomycin plus L-glutamine and recombinant human IL-2 (50 units/ml). The culture plates were incubated 37' C., 5% $CO_2$ for 3 days. 100 μl supernatant/well was removed. 20 μl Promega Cell titer 96 Aqueous One Solution Reagent was added to wells and incubated 4 hours at 37° C. and the wells were assayed by reading the OD at 490 nm.

Figure 3A:
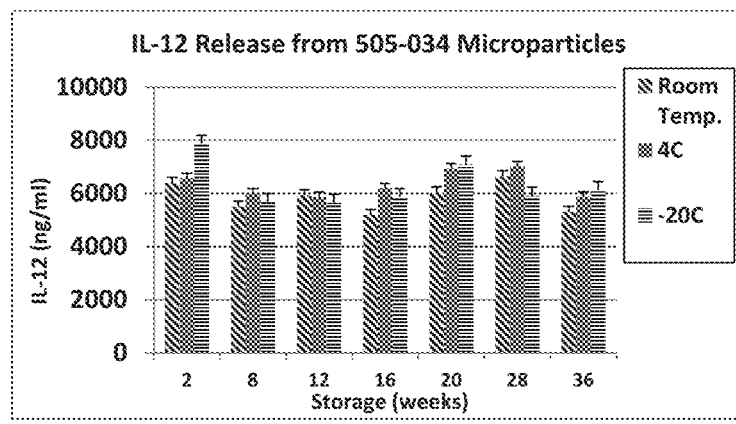
FIGS. 3A and 3B are bar graphs depicting the concentration of released. IL-12 (FIG. 3A y-axis depicts [IL-12] in ng/ml) and bioactivity of released IL-12 (FIG. 3B; y-axis depicts relative activity compared to unstored sample) from the matrices under different storage conditions (room temperature (bar on the far left); 4° C. (middle bar); and −20° C. (bar on the far right)) measured at different time points (x-axis, measured in weeks), relative to freshly prepared compositions containing IL-12 particles.
Figure 3B:
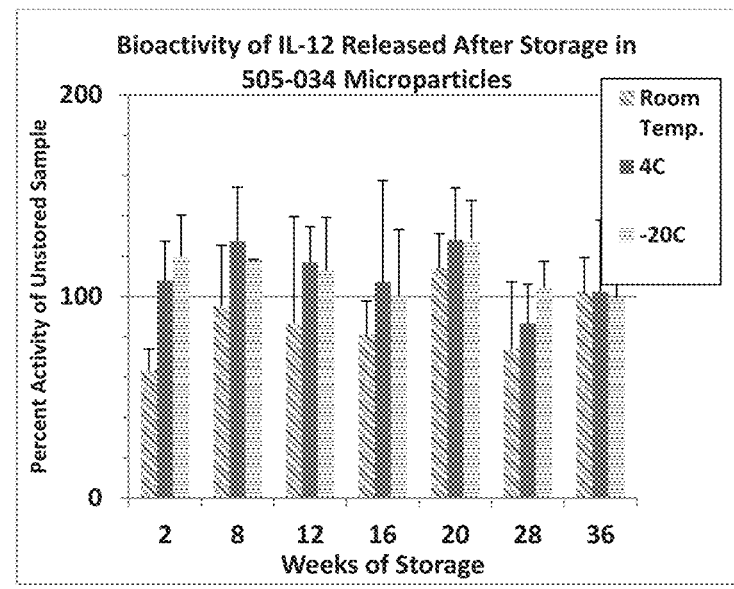

FIGS. 3A-B depict the release and bioactivity of IL-12 after storage for different periods of time.

Results

The IL-12 released from the samples in this test was highly stable in terms of concentration and biological activity over 36 weeks. The only exceptions were the room temperature release samples taken at 2 and 36 weeks in which the observed specific activity was significantly different than the than the control sample (p<0.008). The observed fluctuations were believed to be due to experimental error in these samples.

Example 8

Site Selective Microparticle Delivery

Ten week-old BALB/c mice were fed 30 mg of FITC-labeled bovine serum albumin-loaded (0.025% loading, w/w) microspheres (prepared analogously to the TGF-β example) in 0.1 ml water (single dose). Intestines, mesenteric lymph nodes (MLN), spleen and liver organs were harvested at 15 min, 1 hr, 2.5 hr, 6 hr and 24 hr after gavage and analyzed for the presence of particles by confocal microscopy (green fluorescence, arrow-heads). Peyer's patch dendritic cells were stained with an anti-CD11c antibody (magenta). Lymph nodes or spleens were stained for B-cells (anti-CD220, blue) or Dendritic cells (anti-CD11c, red).

Results

Particles were observed in the Peyer's patch and the mesenteric lymph nodes at all the time points analyzed. No particles could be observed in the colon, liver or spleen at 15 min, 1 hr, 2.5 hr, 6 hr and 24 hr after gavage. Oral formulation microparticles loaded with FITC-BSA were taken up and retained in the Peyer's patches and mesenteric lymph nodes (MLNs) of mice. Microparticles were not detected in the colon, liver or spleen at any time point after feeding. Moreover, when IL-10 loaded microparticles were delivered to mice in bolus doses by oral gavage, IL-10 could not be detected in serum.

Example 9

Anti-Inflammatory Activity of Microparticles 10 week old $APC^{min/+}$ mice, which are prone to develop intestinal polyps as a result of chronic inflammation, were gavaged with either blank control particles or IL-10-loaded particles (0.5 μg IL-10 in 1 mg of particles, prepared analogously to the TGF-β examples) three times a week for four weeks. The intestines were then analyzed for polyp burden.

Results

Six hours after oral gavage, FITC-BSA microparticles were localized from the PPs and MLNs of treated APCmin/+ mice (data not shown).

Figure 4A:
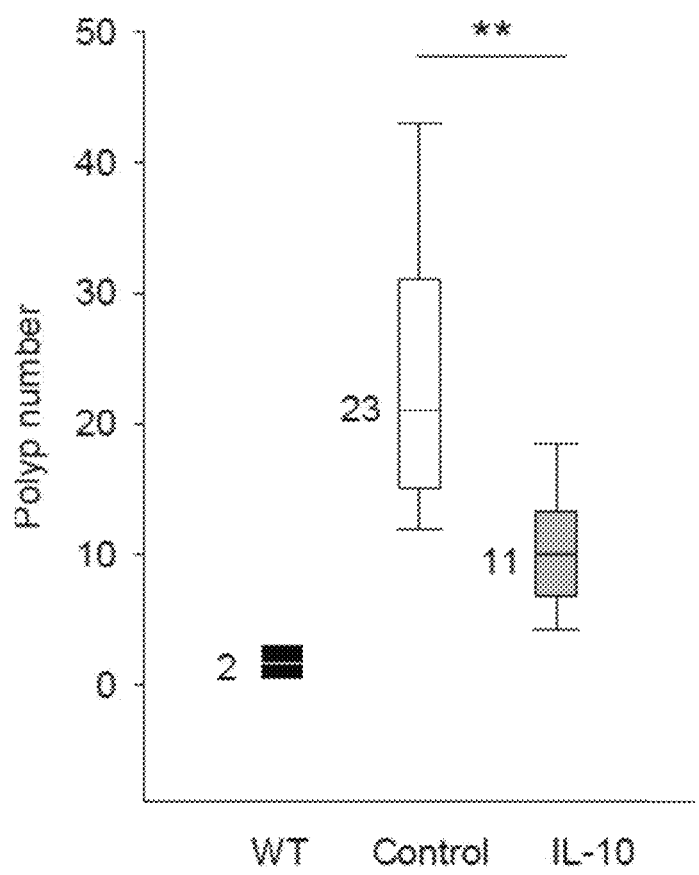
FIGS. 4A-E are graphs depicting the reduced polyp burden (FIG. 4A; y-axis depicts number of polyps), anemia (FIG. 4B; y-axis depicts RBC count ($\times 10^{12}$/L)), splenomegaly (FIG. 4C; y-axis depicts splenic histology score). For FIGS. 4A-C, the left hand dataset corresponds to wild type mice (WT), the middle dataset corresponds to control mice (Control), and the right hand dataset corresponds to mice receiving IL-10 loaded particles (IL-10). For FIG. 4A, numbers indicate the mean; boxes have lines at the median plus lower and upper quartiles, with whiskers extending to show the remaining data (n=5, 9, 9, for WT, Control, IL-10 respectively). For FIG. 4B, n=10, 15, 13 for WT, Control, and IL-10, respectively. For FIG. 4C, Splenic pathology scores (n is identical to panel A) and megakaryocytosis (over 10-12 high power fields, n=3 per group) were quantified.
Figure 4B:
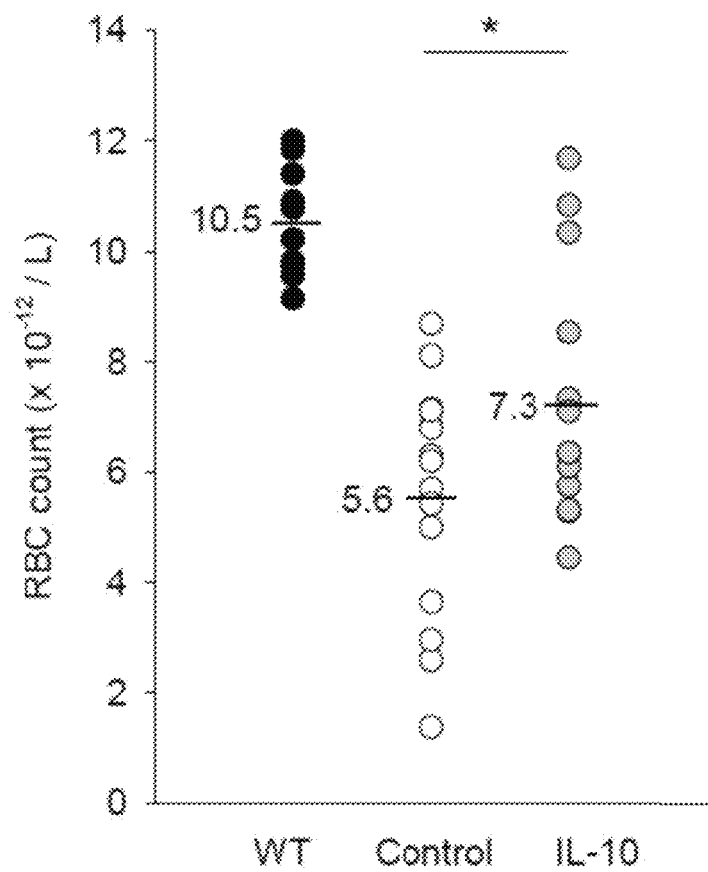
Figure 4D:
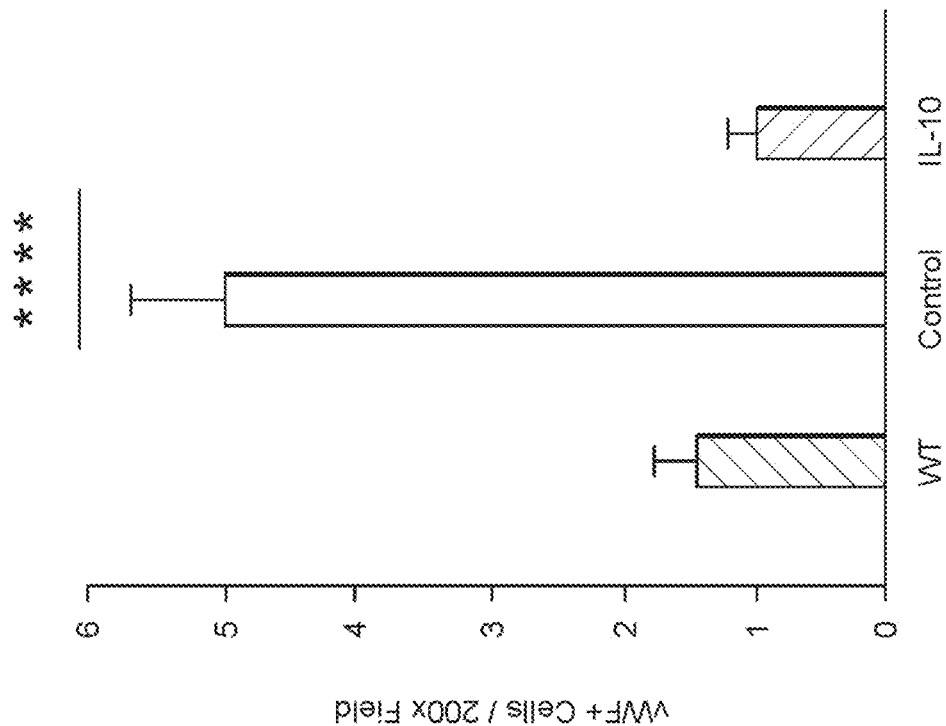
Figure 4C:
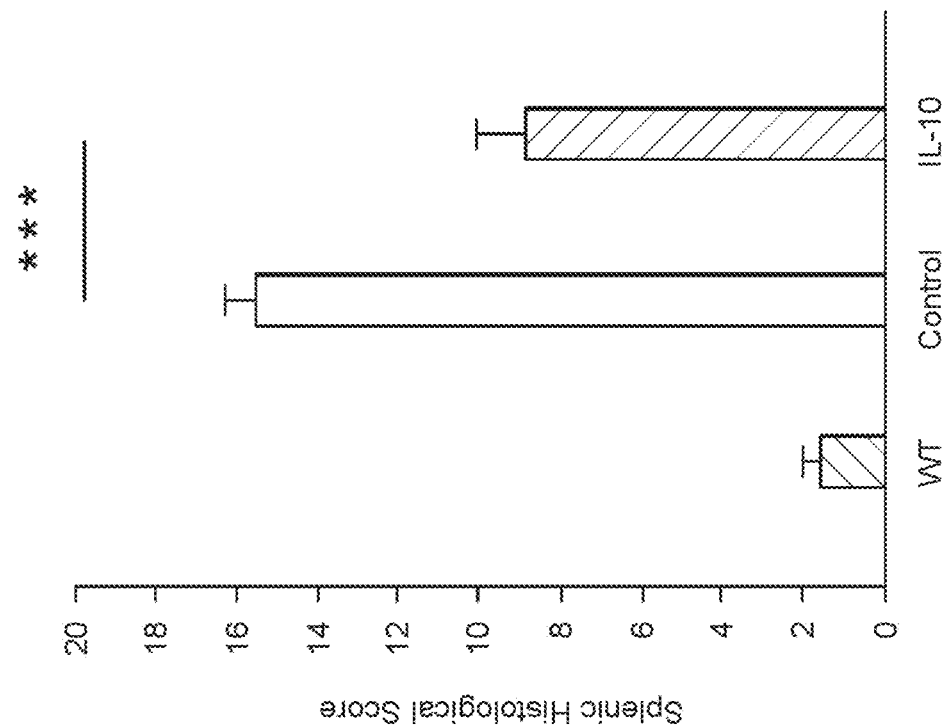

Mice receiving IL-10 exhibited a greater than 2-fold reduction in polyp burden (FIG. 4A). Furthermore, over the course of oral therapy, mice treated with IL-10 exhibited fewer systemic abnormalities, including anemia (FIG. 4B), splenomegaly (FIG. 4C) and weight loss (FIG. 4D) associated with intestinal disease. In FIG. 4C, representative H&E and anti-vWF-stained sections are shown. Megakaryocytes were visualized directly (inset panels). Splenic pathology scores (n is identical to panel A) and megakaryocytosis (over 10-12 high power fields, n=3 per group) were quantified.

Figure 4E:
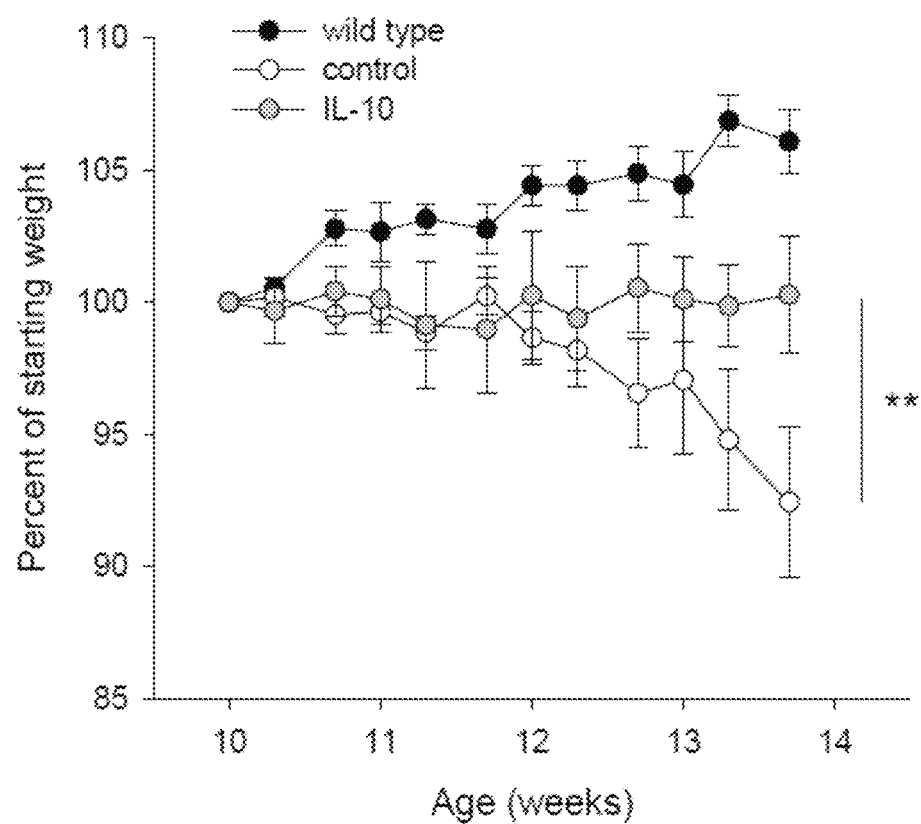
Figure 4F:
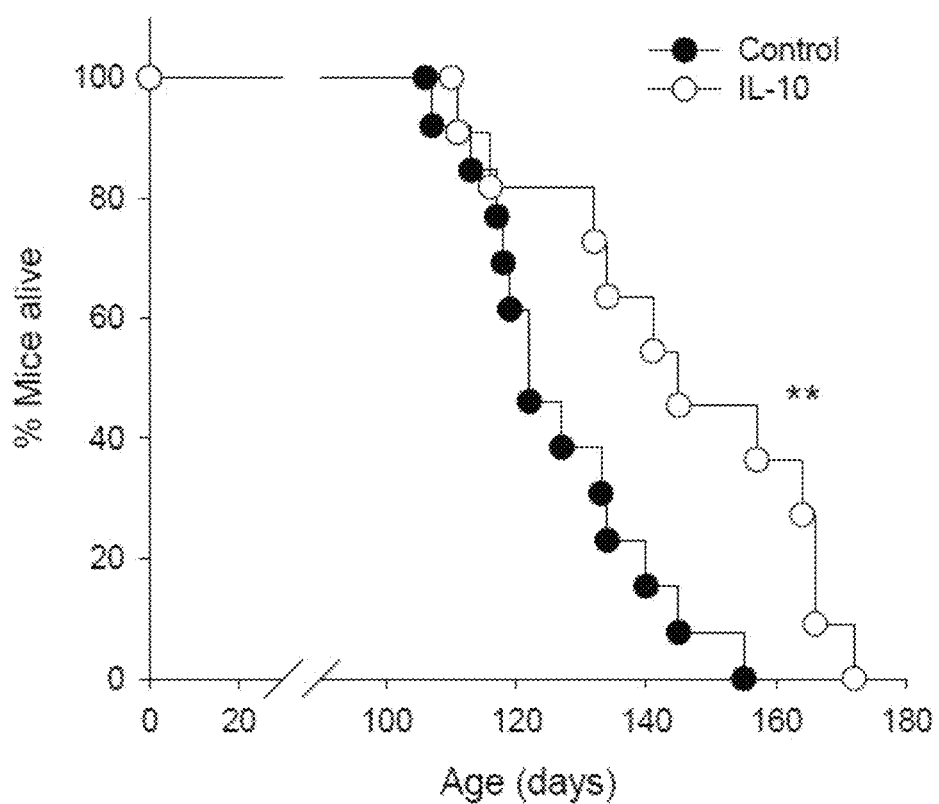

Mice receiving IL-10 also exhibited an extended survival rate relative to control mice (FIG. 4E). Therapy was initiated on day 70.

Increasing the IL-10 dose did not improve therapeutic efficacy (data not shown).

Example 10

IL-17 Expression Profile in Intestinal T-Cells $APC^{min/+}$ mice were crossed with the DEREG murine model of inducible Treg depletion. Ten week-old $APC^{min/+}$ DEREG mice received either mock (PBS) or subtotal Treg depletion (DT), concomitant with either Control or IL-10 microparticle therapy. Disease markers were quantified at the end of the therapeutic period Subtotal Treg depletion resulted in greater than 70% reduction in $FoxP3^+$ cells over 28 days, yet avoided catastrophic myleo- and lymphoproliferative disorders typically seen in mice undergoing total Treg ablation. Subtotal Treg depletion reduced polyp burden, amenia and splenic pathology, and administration of IL-10-loaded particles further enhanced depletion induced effects (see FIGS. 5A-C).

Isolated CD45.2+CD4+CD25+ Treg were mixed with CFSE-labeled CD45.1+ responder cells and applied to an in vivo Treg suppression assay. Responder cells were assessed for generation count, expression of CD44 and total number. The prevalences of IFNγ+CD45.1+CD4+ cells in recipient lymph nodes were also determined. In comparison to cells taken from control $APC^{min/+}$ mice, cells taken from mice treated with IL-10 particles effectively suppressed naïve T-cell proliferation and activation (see FIGS. 6A-6B).

MLN CD45.2+CD4+CD25+ cells were adoptively transferred into 10 week old untreated CD45.2+ APCmin/+ mice. Polyp burdens, RBC levels and prevalences of MLN Th17 cells were assessed in recipients 4 weeks after transfer. Transplantation of cells from IL-10 particle-treated mice into $APC^{min/+}$ mice reduced polyposis, corrected anemia and decreased the prevalence of Th17 cells (see FIGS. 7A-7C).

Example 11

Chemical Integrity as Measured by HPLC

In order to determine the loading protein contained within polymeric microspheres, two different high performance liquid chromatography (HPLC) assays have been developed and validated. The first, a size exclusion chromatography (SEC) assay, utilizes a flow rate of 1.0 ml/min, an injection volume of 10 ul and a run time of 20 minutes. The protein was detected by UV absorbance at 280 nm and compared to reference standards. The second assay, a Reverse Phase (RP) HPLC assay was also used to quantity protein encapsulation.

This method utilizes a flow rate of 0.4 ml/min, an injection volume of 10 ul and a run time of 40 minutes.

The protein was detected by UV absorbance at 280 nm and compared to reference standards. FIGS. 8A and 8B depict chromatograms from IL-12 that was extracted from a matrix particle and IL-12 reference standard, respectively. The overlap indicates that there was no change in chemical integrity.

Example 12

Crystalline Integrity as Measured by PXRD

In order to quantitatively ascertain if the inducing of birefringence had any effect on the polymers amorphous or crystalline alignment and structure, an initial X-Ray Diffraction (XRD) profile was established of the base materials. This was accomplished through the use of the Bruker D-8 Advance X-Ray Powder Diffraction system with DaVinci software (Bruker, Billerica, Mass.). The XRD was equipped with a Cu X-Ray tube operating at 40 kV and 40 mA. The unit is also equipped with a Bruker Vantec-500 Xe-$CO_2$ gas filled detector with a 13.5 cm diameter window set at 20 cm from the goniometer center. The system optics consisted of a polycap with an output beam divergence of 0.25° for Cu and a spot diameter of less than 4.0 mm and a 79 mm long 0.3 mm collimator on the incident beam path. Scans were performed in the following manner.

First, a polymer sample was measured for height using a micrometer. The purpose of this was to ensure that the sample would be co-planar with the aluminum sample stage. To be co-planar the sample must not possess a height greater than 1 mm as this is the limit of what can be subtracted from the Z-plane of the sample stage. Once the sample height was verified to be within tolerance of the XRD constraints, it was placed on the Bruker Powder XRD sample platform using an acrylic disk. The sample was locked in place, and its respective height was entered into the DaVinci XRD software. Once the required data was entered into the software, the XRD scan was run from a 15°-70° 2θ with a virtual step size of 0.02° and a counting time of 30 s per step.

As demonstrated by FIG. 9, the semi-crystalline forms of F127 and PEG 3350 did not substantially change when the polymers were used alone or as part of the particle matrix.

Example 13

Scale Up of Bench Scale Process Using Spray Drying

The bench scale process described herein involving a first step of forming a micronized protein, such as TGFb1, via lyophilization step (step 1), followed by forming a semi-crystalline matrix containing TGFb1 was scaled up using two spray drying processes in place of the lyophilization and precipitation processes.

The same materials were used in the scale up process as the bench scale process. The semicrystalline polymers were PEG 4500, PEG 3350 and Pluronic F-127. TGFβ1 was the protein. However, only 1/10 of the concentration of TGFβ1 encapsulated in the standard bench scale process was used due to its high cost.

In the first spray drying process, i.e. the micronization process, mTGFβ1, Tween 20, Tween 80, PEG 4500, Pluronic F 127, sucrose, glycine, and PVP were mixed with a solvent of water and tert-butyl alcohol. This formulation was fed to an atomizer at suitable liquid feed rate, pressure, inlet and outlet temperature, and drying gas flow rate to form micronized particles of agent.

In the second step, the micronized particles from the first step were mixed with semicrystalline polymers, PEG 3350, and PEG 4500, along with amorphous polymers, PLGA and PLA. The polymers and excipients were dissolved in dichloromethane (DCM), ethanol, and water, while the micronized TGFβ1 was dispersed therein. The resulting formulation that was fed to the second atomizer contained: TGFβ1, Tween 20, Tween 80, PEG 4500, sucrose, glycine, PVP, PLGA, PLA, Pluronic® F-127, and PEG 3350 in DCM, ethanol, and water. This formulation was fed to an atomizer at suitable liquid feed rate, pressure, inlet and outlet temperature, and drying gas flow rate to form matrices containing particles of TGFβ1.

Blank particles were also prepared using this second spray drying step.

The crystallinity of the resulting matrices was evaluated using DSC and PXRD.

FIG. 10 is an overlay of PXRD scans for six batches of blank spray dried particles (SD blank 1, SD blank 2, SD blank 3, SD blank 4, SD blank 5, and SD blank 6), one batch of spray dried particles containing TGFβ1 (SD TGFβ1), blank matrix particles formed by a bench scale process involving a lyophilization step followed by a filtration and recovery step (precipitation) (bench scale blank), Pluronic® F127, PEG 3350, polylactic acid (PLA), and poly(lactide co-glycolide) (PLGA). The PLA and PLGA samples are amorphous, as shown in FIG. 10. The spray dried blank particles and the spray dried particles containing TGFβ1 had crystalline profile to the bench scale blank particles demonstrating that similar products were prepared in the bench scale and scale up methods.

A single Tm was observed at approximately 59° C. in the samples analyzed by DSC, further demonstrating that similar products were prepared in the bench scale and scale up methods.

Example 14

Release Profile from Scale-Up Batch Sample

To verify protein release, an in vitro release assay was performed. Briefly, 10 mg of TGFβ1 particles were suspended in 0.2 mL release buffer (DMEM/F12+10% FCS) and transferred to the wells of a 96-well plate in triplicate. The plate was incubated at 37° C. in 5% $CO_2$, the supernatant replaced daily, and stored at −20° C. for use in TGFβ ELISA (Pierce-Endogen, Thermo-Fisher Scientific Inc, Rockford, Ill.) or bioassay (below).

Bioactivity (24 h) from scale-up batch vs bench scale batch sample. TGFβ biological activity was tested using the TGFβ sensitive mouse lymphoblast cell line HT-2. Cells were plated at 1.5×104 cells/well in complete media containing 15 ng/mL m-IL-4. Standards and samples were added to the wells to produce a final volume of 200 μL/well. The 96 well plates were incubated at 37° C. and 5% $CO_2$ for 67 hours. Cell numbers were determined using Promega Cell titer 96 Aqueous One Solution Reagent (Promega, Madison, Wis.) as per instructions.

Bioactivity released into 24 hour supernatants by scale-up batch sample was 5 to 6-fold lower than typically observed for bench scale preparations. However, this was consistent with a five-fold lower loading ratio used in the scale up preparation.

We claim:

1. A method of making a composition comprising a semi-crystalline matrix comprising (i) microparticles, nanoparticles, or a combination thereof, comprising a protein or peptide and at least one biocompatible polymer, wherein the microparticles, nanoparticles, or a combination thereof is entrapped in the matrix, and (ii) at least one semi-crystalline water soluble polymer, wherein the total amount of the semi-crystalline water soluble polymer in the matrix is at least 65% by weight of the total mass of the matrix, wherein the matrix is characterized by a melting point of at least 40° C., the method comprising:
(a) dissolving at least one semi-crystalline water soluble polymer and at least one biocompatible polymer in an effective amount of a solvent comprising a polar organic solvent, to form a solution, wherein step (a) further comprises adding ethanol as a second organic solvent,
(b) dispersing microparticles, nanoparticles, or a combination thereof, comprising the protein or peptide in the solution of step (a), wherein the semi-crystalline water soluble polymer, the biocompatible polymer, the microparticles, nanoparticles, or a combination thereof, and the solvent form a mixture having a continuous phase and wherein the solvent is the continuous phase, and
(c) performing at least one of the following steps to obtain the composition:
1) introducing the product of step (b) into an effective amount of a non-solvent comprising an organic solvent, or
2) pan coating the product of step (b) in a fluidized bed reactor, and
(d) drying by vacuum or lyophilizing the product of step (c).

2. The method of claim 1, wherein prior to step (b), the protein or peptide is micronized to be in microparticulate or nanoparticulate form.

3. The method of claim 2, wherein the micronization process comprises:
(i) adding the protein or peptide to an aqueous solution, and
(ii) adding the solution of step (i) to a solvent to form a dispersion.

4. The method of claim 1, wherein step (c) involves introducing the product of step (b) into an effective amount of a non-solvent comprising an organic solvent.

5. The method of claim 1, further comprising after step (c) dispersing or suspending the composition in a pharmaceutically acceptable carrier suitable for injection or oral administration.

6. The method of claim 1, wherein the protein or peptide is an antibody.

7. The method of claim 6, wherein the composition is in a powder form.

8. The method of claim 1, wherein the protein or peptide is a cytokine.

9. The method of claim 8, wherein the cytokine is an interleukin.

10. The method of claim 1, wherein the semi-crystalline water soluble polymer in step (a) comprises polyalkylene glycols, poloxamers, polyvinyl alcohols, hydroxyalkyl celluloses, polysorbates, polyoxyethylene stearates, and carrageenans, or a mixture thereof.

11. The method of claim 9, wherein step (a) comprises dissolving two semi-crystalline water soluble polymers in the effective, wherein the semi-crystalline water soluble polymers are polyethylene glycol and a poloxamer.

12. The method of claim 1, wherein the biocompatible polymer is selected from the group consisting of polylactic acid, polyglycolic acid, poly(lactide-co-glycolide), poly(fumaric-co-sebacic anhydride), polycaprolactone, and blends or copolymers thereof.

13. The method of claim 1, wherein the microparticles, nanoparticles, or a combination thereof, have an average particle size between 10 nm and 5 µm, as measured using the Coulter method.

14. The method of claim 1, wherein the microparticles, nanoparticles, or a combination thereof, comprise polyethylene glycol, poloxamer, or both.

15. The method of claim 1, wherein the solvent in step (b) comprises tert-butyl alcohol.

16. The method of claim 1, the composition further comprises an excipient selected from the group consisting of poly(vinyl pyrrolidone), surfactants, sucrose, and glycine.

17. The method of claim 1, wherein step (d) comprises lyophilizing the product of step (c).

18. The method of claim 1, wherein step (c)(1) further comprises filtering the product of step (b).

* * * * *

UNITED STATES PATENT AND TRADEMARK OFFICE
CERTIFICATE OF CORRECTION

| | |
|---|---|
| PATENT NO. | : 11,504,329 B2 |
| APPLICATION NO. | : 16/909493 |
| DATED | : November 22, 2022 |
| INVENTOR(S) | : Edith Mathiowitz et al. |

It is certified that error appears in the above-identified patent and that said Letters Patent is hereby corrected as shown below:

On the Title Page

Item (73), replace:
"(73) Assignees: BROWN UNIVERSITY, Providence, RI (US); THEBAPYX, INC., Buffalo, NY (US)"
With:
--(73) Assignees: BROWN UNIVERSITY, Providence, RI (US); THERAPYX, INC., Buffalo, NY (US)--

Signed and Sealed this
Twenty-eighth Day of February, 2023

Katherine Kelly Vidal
*Director of the United States Patent and Trademark Office*